US009399777B2

(12) United States Patent
Waterhouse et al.

(10) Patent No.: US 9,399,777 B2
(45) Date of Patent: Jul. 26, 2016

(54) METHODS AND MEANS FOR OBTAINING MODIFIED PHENOTYPES

(75) Inventors: Peter Michael Waterhouse, Canberra ACT (AU); Ming-Bo Wang, Canberra ACT (AU)

(73) Assignee: Commonwealth Scientific & Industrial Research Organisation, Campbell (AU)

( * ) Notice: Subject to any disclaimer, the term of this patent is extended or adjusted under 35 U.S.C. 154(b) by 335 days.

(21) Appl. No.: 13/092,645

(22) Filed: Apr. 22, 2011

(65) Prior Publication Data

US 2012/0210469 A1 Aug. 16, 2012

Related U.S. Application Data

(60) Continuation of application No. 11/593,056, filed on Nov. 6, 2006, now abandoned, which is a continuation of application No. 10/152,808, filed on May 23, 2002, now Pat. No. 7,138,565, which is a division of application No. 09/373,720, filed on Aug. 13, 1999, now Pat. No. 6,423,885.

(51) Int. Cl.
*C12N 15/113* (2010.01)
*C12N 15/82* (2006.01)

(52) U.S. Cl.
CPC ........ *C12N 15/8216* (2013.01); *C12N 15/8218* (2013.01); *C12N 15/8283* (2013.01)

(58) Field of Classification Search
None
See application file for complete search history.

(56) References Cited

U.S. PATENT DOCUMENTS

| | | | |
|---|---|---|---|
| 5,034,323 A | 7/1991 | Jorgensen et al. | |
| 5,190,931 A | 3/1993 | Inouye | |
| 5,231,020 A | 7/1993 | Jorgensen et al. | |
| 5,283,184 A | 2/1994 | Jorgensen et al. | |
| 5,814,500 A * | 9/1998 | Dietz | 435/455 |
| 5,908,779 A | 6/1999 | Carmichael et al. | |
| 6,423,885 B1 | 7/2002 | Waterhouse et al. | |
| 6,506,559 B1 * | 1/2003 | Fire et al. | 435/6.16 |
| 7,138,565 B2 | 11/2006 | Waterhouse et al. | |
| 8,183,217 B2 * | 5/2012 | Waterhouse et al. | 514/44 A |

FOREIGN PATENT DOCUMENTS

| | | |
|---|---|---|
| EP | 0223399 | 5/1987 |
| EP | 0240208 | 10/1987 |
| EP | 0467349 | 1/1992 |
| EP | 0647715 | 4/1995 |
| WO | WO89/05852 | 6/1989 |
| WO | WO95/15394 | 6/1995 |
| WO | WO95/34668 | 12/1995 |
| WO | WO98/53083 | 11/1998 |
| WO | WO99/53050 | 10/1999 |

OTHER PUBLICATIONS

Reeder (1994) Mol. Microbiology 12: 11-15.*
Colbert (1992) Genes and Dev. 6: 1940-1949.*
Bramlage et al., "Designing Ribozymes For the Inhibition of Gene Expression", Tibtech, 1998, vol. 16, pp. 434-438, Barking Elsevier Science Publishers, Netherlands.
Covey et al., "Plants Combat Infection by Gene Silencing", Nature, 1997, vol. 385, pp. 781-782, Nature Publishing Group, Hampshire, United Kingdom.
Eckner et al., "Mature mRNA 3' End Formation Stimulates RNA Export From the Nucleus", Embo J., 1991, vol. 10, pp. 3513-3522, Oxford University Press, Oxford, United Kingdom.
Egli et al., "Uncoupling of mRNA 3' cleavage and polyadenylation by expression of a hammerhead ribozyme in yeast", J. Biol. Chem., 1994, vol. 269, pp. 27378-27383, American Society for Biochemistry and Molecular Biology, Bethesda, Maryland.
Donahue, C.P. et al., "Kinetics of Hairpin Ribozyme cleavage in Yeast", RNA, 1997, vol. 3, No. 9, pp. 961-973, Cambridge University Press, U.S.A.
Hamilton et al., "A Transgene With Repeated DNA Causes High Frequency, Post-Transcriptional Suppression of ACC-Oxidase Gene Expression in Tomato", The Plant Journal, 1998, vol. 15, No. 6, pp. 737-746, Blackwell Sciences Ltd., Oxford, United Kingdom.
Haseloff et al., "Simple RNA Enzymes With New and Highly Specific Endoribonuclease Activities", Nature, 1988, vol. 334, pp. 585-591, Nature Publishing Group, Hampshire, UK.
Lee et al., "Post-Transcriptional Gene Silencing of ACC Synthase in Tomato Result Form Cytoplasmic RNA Degardation", The Plant Journal, 1997, vol. 12, No. 5, pp. 1127-1137, Blackwell Sciences Ltd., Oxford, United Kingdom.
Mette et al., "Production of Aberrant Promoter Transcripts Contributes to Methylation and Silencing of Unlinked Homologous Promoters in trans", The EMBO Journal, 1999, vol. 18, pp. 241-248, Oxford University Press, Oxford, United Kingdom.
Metzlaff et al., "RNA-Mediated RNA Degradation and Chalcone Synthase a Silencing in Petunia", Cell, 1997, vol. 88, pp. 845-854, Cell Press, Cambridge, MA.
Miller et al., "A Satellite RNA of Barley Yellow Dwarf Virus Contains a Novel Hammerhead Structure in the Self-Cleavage Domain", Virology, 1991, vol. 183, pp. 711-720, Academic Press, New York, New York.
Rubio et al., "Broad-Spectrum Protection Against Tombusviruses Elicited by Defective Interfering RNAs in Transgenic Plants", J. Virology, 1999, vol. 73, pp. 5070-5078, American Society for Microbiology, Washington DC.
Vaish et al., "Recent Developments in the Hammerhead Ribozyme Field", Nucleic Acids Res., 1998, vol. 26, pp. 5237-5242, IRL Press Limited, Oxford, UK.

(Continued)

*Primary Examiner* — Shubo (Joe) Zhou
*Assistant Examiner* — Stephen Uyeno
(74) *Attorney, Agent, or Firm* — Buchanan Ingersoll & Rooney PC

(57) ABSTRACT

Methods and means are provided for reducing the phenotypic expression of a nucleic acid of interest in eukaryotic cells, particularly in plant cells, by providing aberrant, preferably unpolyadenylated, target-specific RNA to the nucleus of the host cell. Preferably, the unpolyadenylated target-specific RNA is provided by transcription of a chimeric gene comprising a promoter, a DNA region encoding the target-specific RNA, a self-splicing ribozyme and a DNA region involved in 3' end formation and polyadenylation.

48 Claims, 1 Drawing Sheet

(56) References Cited

OTHER PUBLICATIONS

Van Eldik et al., "Silencing of β-1, 3-glucanase Genes in Tobacco Correlates With an Increased Abundance of RNA Degradation Intermediates", Nucleic Acids Res., 1998, vol. 26, pp. 5176-5181, IRL Press Limited, Oxford, UK.

Van Houdt et al., "Post-Transcriptional Silencing of a Neomycin Phosphotransferase II Transsgene Correlates with the Accumulation of Unproductive RNAs and with Increased Cytosine Methylation of 3' Flanking Regions", Plant Journal, 1997, vol. 12, pp. 379-392, Blackwell Science, Ltd., Oxford, UK.

Wassenegger et al., "A Model for RNA-Mediated Gene Silencing in Higher Plants", Plant Mol. Biol., 1998, vol. 37, pp. 349-362, Kluwer Academic Publishers, Netherlands.

Waterhouse et al., "Virus Resistance and Gene Silencing in Plants Can be Induced by Simultaneous Expression of Sense and Antisense RNA". Proc. Natl. Acad. Sci. USA, 1998, vol. 95, pp. 13959-13964, National Academy of Sciences, Washington, DC.

Liu, Zhong et al., "Targeted Nuclear antisense RNA mimics natural antisense-induced degradation of polyoma virus early RNA", Proc. Nat. Acad Sci. U.S.A, 1994, vol. 91, No. 10, pp. 4258-4262, The National Academy of Sciences, U.S.A.

Welch, P.J.et al., "Expression of Ribozymes in gene transfer systems to modulate target RNA levels", Curr. Op Biotech, 1998, vol. 9, No. 5, pp. 486-496, Current Biology Publications, U.S.A.

Liu, Zhong et al., "An Efficient New Method to Inhibit Gene Expression", Molecular Biotechnology, 1994, vol. 21, pp. 107, 109-118, Humana Press, Totowa, NJ.

Thomas et al., "Size Constraints for Targeting Post-Transcriptional gene silencing and for RNA-Directed Methylation in Nicotiana benthamiana using a potato virus X vector", The Plant Journal, 2001, vol. 25, No. 4, pp. 417-425.

Marathe, "*CIS*-Repeat Induced Gene Silencing in Tobaco", Ph.D. Thesis, University of South Carolina, 1997.

J.A. Brussian et al., "An Arabidopsis Mutant with a Reduced Level of *cab140* RNA is a Result of Cosuppression", The Plant Cell, vol. 5, Jun. 1993, p. 667-677, American Society of Plant Physiologists, Rockville, MD, USA.

W.G. Dougherty et al., "Transgenes and Gene Suppression: telling us something new?", Current Opinion in Cell Biology, 1995, vol. 7, p. 399-405; Current Biology, London, UK.

M. Faske et al., "Transgenic Tobacco Plants Expressing Pea Chloroplast *Nmdh* cDNA in Sense and Antisense Orientation", Plant Physiol., 1997, vol. 115, p. 705-715, Am. Soc. of Plant Physiologists, Lancaster, PA.

M.W. Graham et al., "Co-suppression, Anti-sense and Synthetic Viral Resistance: a Common Mechanism!", Symposium 4-3, Abstract for talk given by Michael Graham at the Lorne Genome Conference, Victoria, Australia in Feb. 1996.

M. Katsuki et al, "Conversion of Normal Behavior to Shiverer by Myelin Basic Protein Antisense cDNA in Transgenic Mice", Science, vol. 241, Jul. 29, 1988, p. 593-595, Am. Assn for the Advancement of Science, Washington, DC.

Y.H. Kook et al., "The Effect of Antisense Inhibition of Urokinase Receptor in Human Squamous Cell Carcinoma on Malignancy", The EMBO Journal, vol. 13, No. 17, p. 3938-3991, 1994, Oxford University Press, Oxford, England.

J.A. Lindbo et al., "Virus-Mediated Reprogramming of Gene Expression in Plants", Current Opinion in Plant Biology, vol. 4, p. 181-185, 2001, Elsevier Science Ltd., Amsterdam, Holland.

P. Meyer, "Understanding and Controlling Transgene Expression", TIBTECH, Sep. 1995, vol. 13, p. 332-337, Elsevier Science, Amsterdam, Holland.

P. Meyer, "Homology-Dependent Gene Silencing in Plants", Annu. Rev. Plant Physiol. Plant Mol. Biol., 1996, vol. 47, p. 23-48, Annual Reviews, Inc., Palo Alto, California.

M.K. Montgomery et al., "RNA as a Target of Double-stranded RNA-mediated Genetic Interference in *Caenorhabditis elegans*" Proc. Natl. Acad. Sci. USA, vol. 95, Dec. 1998, p. 15502-15507, the National Academy of Sciences, Washington, D.C.

M.C. Moroni et al, "EGF-R Antisense RNA Blocks Expression of the Epidermal Growth Factor Receptor and Suppresses the Transforming Phenotype of a Human Carcinoma Cell Line", The Journal of Biological Chemistry, vol. 267, No. 5, issue of Feb. 5, 1992, p. 2714-2722, American Society for Biochemistry and Molecular Biology, Baltimore, MD.

C. Napoli et al., "Introduction of a Chimeric Chalcone Synthase Gene into Petunia Results in Reversible Co-Suppression of Homologous Genes *in trans*", the Plant Cell, vol. 2, Apr. 1990, p. 279-289, American Society of Plant Physiologists, Rockville, MD.

J.C. Sanford et al., "The Concept of Parasite-Derived Resistance—Deriving Resistance Genes from the Parasite's own Genome", J. Theor. Biol., 1985, vol. 13, p. 395-405, Academic Press Inc., London, England.

K.W. Savin et al., "Antisense ACC Oxidase RNA Delays Carnation Petal Senescence", HortScience, vol. 30(5), Aug. 1995, p. 970-972, HortScience is a publication of the American Society for Horticulture Science.

W. Schiebel et al., "RNA-directed RNA Polymerase from Tomato Leaves", The Journal of Biological Chemistry, vol. 268, No. 16, Jun. 5, 1993, p. 11858-11867, American Society for Biochemistry and Molecular Biology, Inc., Baltimore, MD.

R.E. Sheehy et al., "Reduction of Polygalacturonase Activity in Tomato Fruit by Antisense RNA", Proc Natl Acad. Sci, USA, vol. 85, Dec. 1988, p. 8805-8809, the National Academy of Sciences, Washington, D.C.

B.A. Sullenger et al, "Analysis of *trans*-Acting Response Decoy RNA-Mediated Inhibition of Human Immunodeficiency Virus Type 1 Transactivation", Journal of Virology, Dec. 1991, vol. 65, No. 12, p. 6811-6816, American Society for Microbiology, Washington D.C.

S. Swaney et al., "RNA-Mediated Resistance with Nonstructural Genes from the Tobacco Etch Virus Genome", MPMI vol. 8, No. 6, 1995, p. 1005-1011, The American Phytopathological Society, St. Paul, Minnesota.

R. Van Blokland et al, "Transgene-mediated Suppression of Chalcone Synthase Expression in *Petunia hybrida* Results from an increase in RNA Turnover", The Plant Journal, 1994, vol. 6, No. 6, p. 861-877, Blackwell Sciences, Oxford, England.

A.R. van der Krol et al., "Flavonoid Genes in Petunia: Addition of a Limited Number of Gene Copies May Lead to a Suppression of Gene Expression", The Plant Cell, vol. 2, Apr. 1990, p. 291-299, American Society of Plant Physiologists, Rockville, MD.

Heard et al., Nucl. Acids. Res., 1995, vol. 23, pp. 1970-1976.

Doelling et al., PNAS, 1995, vol. 8, pp. 683-692.

Decision on Appeal for Reexamination Control 90/007,247 and 90/008,096 mailed on Sep. 29, 2010.

* cited by examiner

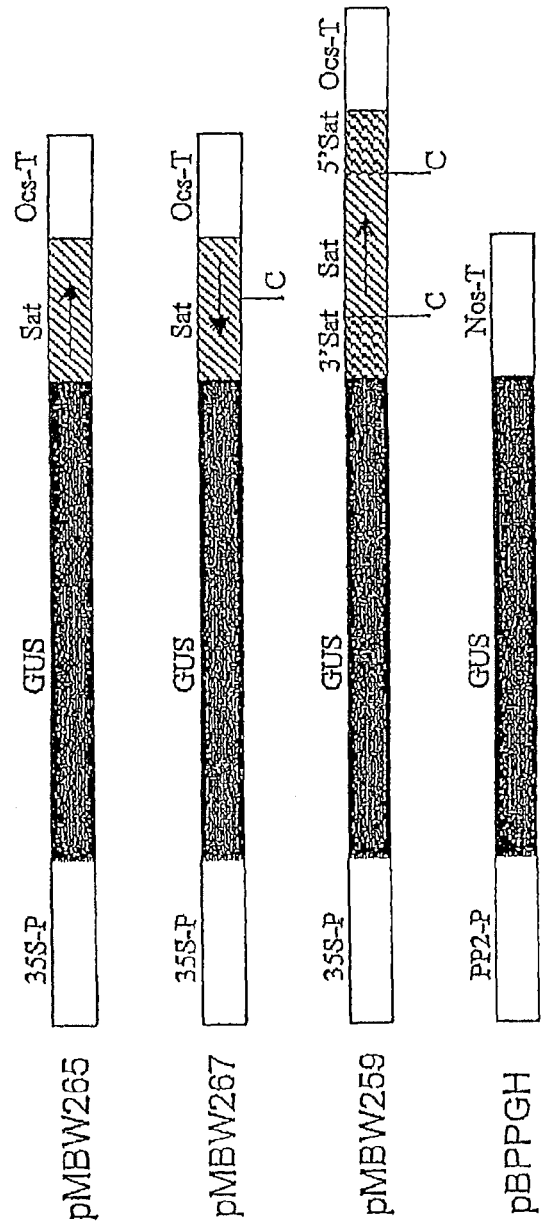

METHODS AND MEANS FOR OBTAINING MODIFIED PHENOTYPES

CROSS REFERENCE TO RELATED APPLICATIONS

This application is a Continuation Application of U.S. patent application Ser. No. 11/593,056, filed Nov. 6, 2006, which is a Continuation Application of U.S. patent application Ser. No. 10/152,808, filed May 23, 2002, now U.S. Pat. No. 7,138,565, which is a Divisional Application of U.S. application Ser. No. 09/373,720, filed on Aug. 13, 1999, now U.S. Pat. No. 6,423,885, all of which are incorporated herein by reference in their entireties.

FIELD OF THE INVENTION

The invention relates to methods for reducing the phenotypic expression of a nucleic acid of interest in plant cells by providing aberrant RNA molecules, preferably unpolyadenylated RNA molecules comprising at least one target specific nucleotide sequence homologous to the nucleic acid of interest, preferably a sense strand, into the nucleus of plant cells. The target-specific unpolyadenylated RNA molecules may be provided by introduction of chimeric DNAs which when transcribed under control of conventional promoter and 3' end formation and polyadenylation regions yield RNA molecules wherein at least the polyadenylation signal may be removed by the autocatalytic activity of a self-splicing ribozyme comprised within the transcribed RNA molecules. Also provided are plant cells comprising such RNA molecules or chimeric DNA encoding such RNA molecules, as well as plants. Similar methods and means for reducing the phenotypic expression of a nucleic acid by co-suppression in eukaryotic cells are provided.

BACKGROUND OF THE INVENTION

Post-transcriptional gene silencing (PTGS) or co-suppression, is a common phenomenon associated with transgenes in transgenic plants. PTGS results in sequence-specific removal of the silenced transgene RNA as well as homologous endogenous gene RNA or viral RNA. It is characterized by low steady-state mRNA levels with normal (usually high) rates of nuclear transcription of transgenes being maintained. There are a number of common features or characteristics for PTGS. PTGS is
- sequence-specific;
- systemically transmissible;
- often associated with the presence of multiple copies of transgenes or with the use of strong promoters;
- frequently correlated with the presence of repetitive DNA structures, including inverted repeat T-DNA insertion patterns;
- often accompanied by de novo DNA methylation in the transcribed region, and
- may be meiotically reset.

A number of hypothetical models have been proposed to explain PTGS (see e.g. Wassenegger and Pélissier, 1998). Typically, these models suggest the involvement of a host encoded enzyme (RNA-directed RNA polymerase (RdRP)) which is proposed to use aberrant RNA as templates to synthesize small copy RNA molecules (cRNA). These cRNAs would then hybridize with the target mRNA to form duplex structures, thereby rendering the mRNA susceptible to degradation by endoribonucleases. So far, there has been no direct evidence that RdRP is involved in PTGS in plants.

An important question arising from the existing models is what type of RNA is the aberrant RNA that would be used as a template by RdRP, and in which cellular compartment RdRP would function.

Several reports have described the accumulation of unproductive or unpolyadenylated transgene RNA in plants which are post-transcriptionally silenced (Lee et al. 1997; van Eldik et al. 1998; Covey et al., 1997; van Houdt et al., 1997; Metzlaff et al.; 1997).

The following documents relate to methods and means for regulating or inhibiting gene expression in a cell.

U.S. Pat. No. 5,190,131 and EP 0 467 349 A1 describe methods and means to regulate or inhibit gene expression in a cell by incorporating into or associating with the genetic material of the cell a non-native nucleic acid sequence which is transcribed to produce an mRNA which is complementary to and capable of binding to the mRNA produced by the genetic material of that cell.

EP 0 223 399 A1 describes methods to effect useful somatic changes in plants by causing the transcription in the plant cells of negative RNA strands which are substantially complementary to a target RNA strand. The target RNA strand can be a mRNA transcript created in gene expression, a viral RNA, or other RNA present in the plant cells. The negative RNA strand is complementary to at least a portion of the target RNA strand to inhibit its activity in vivo.

EP 0 240 208 describes a method to regulate expression of genes encoded for in plant cell genomes, achieved by integration of a gene under the transcriptional control of a promoter which is functional in the host and in which the transcribed strand of DNA is complementary to the strand of DNA that is transcribed from the endogenous gene(s) one wishes to regulate.

EP 0 647 715 A1 and U.S. Pat. Nos. 5,034,323, 5,231,020 and 5,283,184 describe methods and means for producing plants exhibiting desired phenotypic traits, by selecting transgenotes that comprise a DNA segment operably linked to a promoter, wherein transcription products of the segment are substantially homologous to corresponding transcripts of endogenous genes, particularly endogenous flavonoid biosynthetic pathway genes.

Waterhouse et al. 1998 describe that virus resistance and gene silencing in plants can be induced by simultaneous expression of sense and anti-sense RNA. The sense and anti-sense RNA may be located in one transcript that has self-complementarity.

Hamilton et al. 1998 describes that a transgene with repeated DNA, i.e. inverted copies of its 5' untranslated region, causes high frequency, post-transcriptional suppression of ACC-oxidase expression in tomato.

WO 98/53083 describes constructs and methods for enhancing the inhibition of a target gene within an organism which involve inserting into the gene silencing vector an inverted repeat sequence of all or part of a polynucleotide region within the vector.

WO 95/34688 describes methods for cytoplasmic inhibition of gene expression and provides genetic constructs for the expression of inhibitory RNA in the cytoplasm of eukaryotic cells. The inhibitory RNA may be an anti-sense or a co-suppressor RNA. The genetic constructs are capable of replicating in the cytoplasm of a eukaryotic cell and comprise a promoter region, which may be a plant virus subgenomic promoter in functional combination with the RNA encoding region.

WO95/15394 and U.S. Pat. No. 5,908,779 describe a method and construct for regulating gene expression through inhibition by nuclear antisense RNA in (mouse) cells. The construct comprises a promoter, antisense sequences, and a cis- or trans-ribozyme which generates 3'-ends independently of the polyadenylation machinery and thereby inhibits the transport of the RNA molecule to the cytoplasm.

SUMMARY OF THE INVENTION

The present invention provides a method for reducing the phenotypic expression of a nucleic acid of interest, which is normally capable of being expressed in a plant cell, the method comprising the step of providing to the nucleus of that plant cell aberrant RNA comprising a target-specific nucleotide sequence, preferably unpolyadenylated RNA comprising a target specific nucleotide sequence, particularly by producing aberrant RNA such as unpolyadenylated RNA by transcription of a chimeric DNA comprised within the plant cell, the chimeric DNA comprising a plant-expressible promoter operably linked to a target specific DNA region encoding that RNA and optionally further comprising a DNA region involved in 3' end formation and polyadenylation, preceded by a self-splicing ribozyme encoding DNA region.

The invention also provides a method for reducing the phenotypic expression of a nucleic acid of interest, which is normally capable of being expressed in a plant cell, the method comprising the step of introducing into the nuclear genome of the plant cell a chimeric DNA to generate a transgenic plant cell, the chimeric DNA comprising the following operably linked parts:
  a plant-expressible promoter region, preferably a constitutive promoter or an inducible promoter or a tissue-specific promoter;
  a target-specific DNA region encoding a target-specific nucleotide sequence, preferably a target-specific DNA region comprising a nucleotide sequence of at least 10 consecutive nucleotides having at least about 70% sequence identity to about 100% sequence identity to the nucleic acid of interest or comprising a nucleotide sequence of at least 10 consecutive nucleotides having at least about 70% sequence identity to about 100% sequence identity to the complement of said nucleic acid of interest;
  a DNA region encoding a self-splicing ribozyme, preferably a self-splicing ribozyme comprising a cDNA copy of a self-splicing ribozyme from avocado sunblotch viroid, peach latent mosaic viroid, Chrysanthemum chlorotic mottle viroid, carnation stunt associated viroid, Newt satellite 2 transcript, *Neurospora* VS RNA, barley yellow dwarf virus satellite RNA, arabis mosaic virus satellite RNA, chicory yellow mottle virus satellite RNA S1, lucerne transient streak virus satellite RNA, tobacco ringspot virus satellite RNA, subterranean clover mottle virus satellite RNA, solanum nodiflorum mottle virus satellite RNA, velvet tobacco mottle virus satellite RNA, Cherry small circular viroid-like RNA or hepatitis delta virus RNA, particularly a DNA region comprising the nucleotide sequence of SEQ ID No 1 or SEQ ID No 2 or a ribozyme-effective part thereof; and
  a) a DNA region involved in 3' end formation and polyadenylation;
wherein said chimeric DNA when transcribed produces a first RNA molecule comprising a target specific nucleotide sequence and a self-splicing ribozyme, which when cleaved by autocatalysis produces a second RNA molecule comprising a target specific nucleotide sequence wherein the 3' end of the first RNA molecule comprising the polyadenylation site has been removed. Optionally, a transgenic plant may be regenerated from the transgenic plant cell. Preferably, the DNA region encoding a self-splicing ribozyme is located immediately upstream of the DNA region involved in 3' end formation and polyadenylation.

It is another objective of the invention to provide a chimeric DNA molecule for reducing the phenotypic expression of a nucleic acid of interest, which is normally capable of being expressed in a plant cell, comprising
  a plant-expressible promoter region, preferably a constitutive promoter or an inducible promoter or a tissue-specific promoter;
  a target-specific DNA region encoding a target-specific nucleotide sequence, preferably a target-specific DNA region comprising a nucleotide sequence of at least 10 consecutive nucleotides having at least about 70% sequence identity to about 100% sequence identity to the nucleic acid of interest or comprising a nucleotide sequence of at least 10 consecutive nucleotides having at least about 70% sequence identity to about 100% sequence identity to the complement of said nucleic acid of interest;
  a DNA region encoding a self-splicing ribozyme, preferably a self-splicing ribozyme comprising a cDNA copy of a self-splicing ribozyme from avocado sunblotch viroid, peach latent mosaic viroid, Chrysanthemum chlorotic mottle viroid, carnation stunt associated viroid, Newt satellite 2 transcript, *Neurospora* VS RNA, barley yellow dwarf virus satellite RNA, arabis mosaic virus satellite RNA, chicory yellow mottle virus satellite RNA S1, lucerne transient streak virus satellite RNA, tobacco ringspot virus satellite RNA, subterranean clover mottle virus satellite RNA, solanum nodiflorum mottle virus satellite RNA, velvet tobacco mottle virus satellite RNA, Cherry small circular viroid-like RNA or hepatitis delta virus RNA, particularly a DNA region comprising the nucleotide sequence of SEQ ID No 1 or SEQ ID No 2 or a ribozyme-effective part thereof; and
  a DNA region involved in 3' end formation and polyadenylation;
wherein said chimeric DNA when transcribed produces a first RNA molecule comprising a target specific nucleotide sequence and a self-splicing ribozyme, which when cleaved by autocatalysis produces a second RNA molecule comprising a target specific nucleotide sequence wherein the 3' end of the first RNA molecule comprising the polyadenylation site has been removed. Preferably, the DNA region encoding a self-splicing ribozyme is located immediately upstream of the DNA region involved in 3' end formation and polyadenylation.

It is yet another objective of the invention to provide plant cells and plants comprising a nucleic acid of interest which is normally capable of being phenotypically expressed, further comprising a chimeric DNA, preferably stably integrated into the nuclear genome, comprising
  a plant-expressible promoter region, preferably a constitutive promoter or an inducible promoter or a tissue-specific promoter;
  a target-specific DNA region encoding a target-specific nucleotide sequence, preferably a target-specific DNA region comprising a nucleotide sequence of at least 10 consecutive nucleotides having at least about 70% sequence identity to about 100% sequence identity to the nucleic acid of interest or comprising a nucleotide sequence of at least 10 consecutive nucleotides having at least about 70% sequence identity to about 100% sequence identity to the complement of said nucleic acid of interest;

a DNA region encoding a self-splicing ribozyme, preferably a self-splicing ribozyme comprising a cDNA copy of a self-splicing ribozyme from avocado sunblotch viroid, peach latent mosaic viroid, Chrysanthemum chlorotic mottle viroid, carnation stunt associated viroid, Newt satellite 2 transcript, *Neurospora* VS RNA, barley yellow dwarf virus satellite RNA,arabis mosaic virus satellite RNA, chicory yellow mottle virus satellite RNA S1, lucerne transient streak virus satellite RNA, tobacco ringspot virus satellite RNA, subterranean clover mottle virus satellite RNA, solanum nodiflorum mottle virus satellite RNA, velvet tobacco mottle virus satellite RNA, Cherry small circular viroid-like RNA or hepatitis delta virus RNA, particularly a DNA region comprising the nucleotide sequence of SEQ ID No 1 or SEQ ID No 2 or a ribozyme-effective part thereof; and
a DNA region involved in 3' end formation and polyadenylation;

wherein said chimeric DNA when transcribed produces a first RNA molecule comprising a target specific nucleotide sequence and a self-splicing ribozyme, which when cleaved by autocatalysis produces a second RNA molecule comprising a target specific nucleotide sequence wherein the 3' end of the first RNA molecule comprising the polyadenylation site has been removed. The invention also provides a method for identifying a phenotype associated with the expression of a nucleic acid of interest in a plant cell, the method comprising:
1) selecting within the nucleic acid of interest a target sequence of at least 10 consecutive nucleotides;
2) introducing a chimeric DNA into the nucleus of a suitable plant host cell comprising the nucleic acid of interest, the chimeric DNA comprising the following operably linked DNA fragments:
   a) a plant-expressible promoter region;
   b) a target-specific DNA region comprising a nucleotide sequence of at least about 70% to about 100% sequence identity to said target sequence or to the complement of said target sequence; followed by
   c) a DNA region encoding a self-splicing ribozyme located immediately upstream of
   d) a DNA region involved in 3' end formation and polyadenylation;
3) observing the phenotype by a suitable method.

Yet another objective of the invention is to provide a method for reducing the phenotypic expression of a nucleic acid of interest, which is normally capable of being expressed in a eukaryotic cell, the method comprising the step of providing to the nucleus of said eukaryotic cell aberrant RNA, preferably unpolyadenylated RNA, comprising a target specific nucleotide sequence of at least 10 consecutive nucleotides with at least about 70% sequence identity to about 100% sequence identity to the nucleotide sequence of the nucleic acid of interest, particularly by producing aberrant RNA such as unpolyadenylated RNA by transcription of a chimeric DNA comprised within the eukaryotic cell, the chimeric DNA comprising a plant-expressible promoter operably linked to a target specific DNA region encoding that RNA and optionally further comprising a DNA region involved in 3' end formation and polyadenylation, preceded by a self-splicing ribozyme encoding DNA region.

Still another objective of the invention is to provide a method for reducing the phenotypic expression of a nucleic acid of interest, which is normally capable of being expressed in a eukaryotic cell, comprising the step of introducing into the nuclear genome of the eukaryotic cell a chimeric DNA to generate a transgenic plant cell, comprising the following operably linked parts:
a) a promoter region functional in the eukaryotic cell;
b) a target-specific DNA region comprising nucleotide sequence of at least 10 consecutive nucleotides with at least about 70% sequence identity to about 100% sequence identity to the nucleotide sequence of the nucleic acid of interest;
c) a DNA region encoding a self-splicing ribozyme; and
d) a DNA region involved in 3' end formation and polyadenylation wherein the chimeric DNA when transcribed produces a first RNA molecule comprising a target specific nucleotide sequence and a self-splicing ribozyme, which when cleaved by autocatalysis produces a second RNA molecule comprising a target specific nucleotide sequence wherein the 3' end of the first RNA molecule comprising the polyadenylation site has been removed.

The invention also provides a eukaryotic cell comprising a nucleic acid of interest, normally capable of being phenotypically expressed, further comprising a chimeric DNA comprising the following operably linked parts:
a promoter region functional in the eukaryotic cell;
a target-specific DNA region comprising nucleotide sequence of at least 10 consecutive nucleotides with at least about 70% sequence identity to about 100% sequence identity to the nucleotide sequence of the nucleic acid of interest;
a DNA region encoding a self-splicing ribozyme; and
a DNA region involved in 3' end formation and polyadenylation wherein said chimeric DNA when transcribed in the eukaryotic cell produces a first RNA molecule comprising a target specific nucleotide sequence and a self-splicing ribozyme, which when cleaved by autocatalysis produces a second RNA molecule comprising a target specific nucleotide sequence wherein the 3' end of the first RNA molecule comprising the polyadenylation site has been removed, as well as non-human eukaryotic organisms comprising or consisting essentially of such eukaryotic cells.

BRIEF DESCRIPTION OF THE FIGURES

FIG. 1. Schematic representation of the ribozyme-containing GUS chimeric gene (pMBW267 and pMBW259) the control construct (pMBW 265) and the GUS chimeric gene used for supertransformation (pBPPGH). 35S-P: CaMV 35S promoter; GUS: region encoding β-glucuronidase; SAT: cDNA copy of the satellite RNA of Barley Yellow Dwarf Virus (BYDV) in positive strand orientation (→) or in minus strand orientation (←); Ocs-T: region from the octopine synthase gene from *Agrobacterium* involved in 3' end formation and polyadenylation; 3' Sat: cDNA copy of the 3' end of the satellite RNA of BYDV; 5' SAT: cDNA copy of the 5' end of the satellite RNA of BYDV; PP2-P: 1.3 kb promoter region of a gene encoding the cucurbit phloem protein PP2; Nos-T: region from the nopaline synthase gene from *Agrobacterium* involved in 3' end formation and polyadenylation; C: autocatalytic cleavage site in the RNA molecule transcribed from the chimeric gene.

DETAILED DESCRIPTION OF THE PREFERRED EMBODIMENTS OF THE INVENTION

Although gene-silencing, either by anti-sense RNA or through co-suppression using sense RNA, is a commonly observed phenomenon in transgenic research, the intentional generation of gene-silenced transgenic eukaryotic cells and transgenic organisms, particularly plant cells and plants, still faces a number of problems. In particular the efficiency of gene-silencing is still amenable to improvement, both in number of transgenic lines exhibiting the phenomenon as well as in the level of reduction of transcription and ultimately the phenotypic expression of particular nucleic acid of interest in a particular transgenic line.

A number of improved methods for gene-silencing have already been described, e.g. the simultaneous use in one cell of anti-sense and sense RNA targeted to the nucleic acid of interest, preferably co-located on one transcript exhibiting self-complementarity. Novel methods for increasing the efficiency of gene-silencing, preferably gene-silencing through co-suppression in a eukaryotic cell or organism, preferably plant cell or plant, and means therefore, are described in the different embodiments provided by the specification and claims.

The current invention is based on the unexpected observation by the inventors, that the provision or the introduction of aberrant target-specific RNA, preferably unpolyadenylated target-specific RNA, particularly an aberrant target-specific RNA comprising a nucleotide sequence essentially identical to the nucleic acid of interest in sense orientation, into the nucleus of a cell of a eukaryotic organism, particularly a cell of plant, resulted in an efficient reduction of the expression of the nucleic acid of interest, both in the level of reduction as well as in the number of transgenic lines exhibiting gene-silencing. The understanding of hypothetical mechanisms through which gene-silencing, particularly PTGS, is supposed to proceed did not allow to predict that among all variables potentially involved in initiation and maintenance of gene-silencing, the selection of this one parameter—i.e. providing aberrant, preferably unpolyadenylated RNA—would have been sufficient to significantly increase the efficiency of gene-silencing, particularly gene-silencing through co-suppression.

In one embodiment of the invention, a method is provided for reducing the phenotypic expression of a nucleic acid of interest, which is normally capable of being expressed in a plant cell, comprising the step of providing aberrant RNA such as unpolyadenylated RNA which includes a target-specific nucleotide sequence to the nucleus of that plant cell. Conveniently, the aberrant RNA such as unpolyadenylated RNA including the target-specific nucleotide sequence may be produced by transcription of a chimeric DNA or chimeric gene comprised within the plant cell, preferably incorporated, particularly stably integrated into the nuclear genome of the plant cell. In a particularly preferred embodiment, the aberrant RNA is unpolyadenylated RNA which still exhibits other modifications characteristic of mRNA, such as, but not limited to, the presence of a cap-structure at the 5' end.

As used herein, the term "expression of a gene" refers to the process wherein a DNA region which is operably linked to appropriate regulatory regions, particularly to a promoter region, is transcribed into an RNA which is biologically active i.e., which is either capable of interaction with another nucleic acid or which is capable of being translated into a polypeptide or protein. A gene is said to encode an RNA when the end product of the expression of the gene is biologically active RNA, such as e.g. an antisense RNA, a ribozyme or a replicative intermediate. A gene is said to encode a protein when the end product of the expression of the gene is a protein or polypeptide.

A nucleic acid of interest is "capable of being expressed", when said nucleic acid, when introduced in a suitable host cell, particularly in a plant cell, can be transcribed (or replicated) to yield an RNA, and/or translated to yield a polypeptide or protein in that host cell.

The term "gene" means any DNA fragment comprising a DNA region (the "transcribed DNA region") that is transcribed into a RNA molecule (e.g., a mRNA) in a cell operably linked to suitable regulatory regions, e.g., a plant-expressible promoter. A gene may thus comprise several operably linked DNA fragments such as a promoter, a 5' leader sequence, a coding region, and a 3' region comprising a polyadenylation site. A plant gene endogenous to a particular plant species (endogenous plant gene) is a gene which is naturally found in that plant species or which can be introduced in that plant species by conventional breeding. A chimeric gene is any gene which is not normally found in a plant species or, alternatively, any gene in which the promoter is not associated in nature with part or all of the transcribed DNA region or with at least one other regulatory region of the gene.

As used herein, "phenotypic expression of a nucleic acid of interest" refers to any quantitative trait associated with the molecular expression of a nucleic acid in a host cell and may thus include the quantity of RNA molecules transcribed or replicated, the quantity of post-transcriptionally modified RNA molecules, the quantity of translated peptides or proteins, the activity of such peptides or proteins.

A "phenotypic trait" associated with the phenotypic expression of a nucleic acid of interest refers to any quantitative or qualitative trait, including the trait mentioned, as well as the direct or indirect effect mediated upon the cell, or the organism containing that cell, by the presence of the RNA molecules, peptide or protein, or posttranslationally modified peptide or protein. The mere presence of a nucleic acid in a host cell, is not considered a phenotypic expression or a phenotypic trait of that nucleic acid, even though it can be quantitatively or qualitatively traced. Examples of direct or indirect effects mediated on cells or organisms are, e.g., agronomically or industrial useful traits, such as resistance to a pest or disease; higher or modified oil content etc.

As used herein, "reduction of phenotypic expression" refers to the comparison of the phenotypic expression of the nucleic acid of interest to the eukaryotic cell in the presence of the RNA or chimeric genes of the invention, to the phenotypic expression of the nucleic acid of interest in the absence of the RNA or chimeric genes of the invention. The phenotypic expression in the presence of the chimeric RNA of the invention should thus be lower than the phenotypic expression in absence thereof, preferably be only about 25%, particularly only about 10%, more particularly only about 5% of the phenotypic expression in absence of the chimeric RNA, especially the phenotypic expression should be completely inhibited for all practical purposes by the presence of the chimeric RNA or the chimeric gene encoding such an RNA.

A reduction of phenotypic expression of a nucleic acid where the phenotype is a qualitative trait means that in the presence of the chimeric RNA or gene of the invention, the phenotypic trait switches to a different discrete state when compared to a situation in which such RNA or gene is absent. A reduction of phenotypic expression of a nucleic acid may thus, a.o., be measured as a reduction in transcription of (part of) that nucleic acid, a reduction in translation of (part of) that nucleic acid or a reduction in the effect the presence of the transcribed RNA(s) or translated polypeptide(s) have on the eukaryotic cell or the organism, and will ultimately lead to altered phenotypic traits. It is clear that the reduction in phenotypic expression of a nucleic acid of interest, may be accompanied by or correlated to an increase in a phenotypic trait.

As used herein "a nucleic acid of interest" or a "target nucleic acid" refers to any particular RNA molecule or DNA sequence which may be present in a eukaryotic cell, particularly a plant cell.

As used herein "aberrant RNA" refers to polyribonucleotide molecules which have characteristic differing from mRNA molecules normally found in that cell. The different characteristics include but are not limited to the absence or removal of a 5' cap structure, presence of persistent introns e.g. introns which have been modified in their splice sites so as to prevent splicing, or the absence of the polyA tail normally found associated with the mRNA ("unpolyadenylated RNA").

The term "target-specific nucleotide sequence" as used herein, refers to a nucleotide sequence (either DNA or RNA nucleotide sequence depending on the context) which can reduce the expression of the target nucleic acid of interest by gene-silencing. Preferably, only the expression of the target nucleic acid or gene, or nucleic acids or genes comprising essentially similar nucleotide sequence is reduced.

Preferably the target-specific nucleotide sequence comprises a nucleotide sequence corresponding to the "sense" nucleotide sequence of the nucleic acid or gene of interest. In other words, a target-specific sense nucleotide sequence may be essentially similar to part of an RNA molecule transcribed or produced from the nucleic acid or gene of interest or to parts of the nucleic acid or gene of interest controlling the production of that transcribed or produced RNA molecule, when read in the same 5' to 3' direction as the transcribed or produced RNA molecule.

Preferably, the target specific nucleotide sequence corresponds to part of a nucleic acid region from which RNA is produced, particularly a region which is transcribed and translated. It is particularly preferred that the target sequence corresponds to one or more consecutive exons, more particularly is located within a single exon of a coding region. However, the target specific nucleotide sequence may also be corresponding to untranslated regions of the RNA molecule produced from the nucleic acid or gene of interest. Moreover, in the light of a recent publication by Mette et al. (1999), it is expected that the target specific nucleotide sequence may also correspond to the regions controlling the production or transcription of RNA from the nucleotide or gene of interest, such as the promoter region.

The length of the sense target-specific nucleotide sequence may vary from about 10 nucleotides (nt) up to a length equaling the length (in nucleotides) of the target nucleic acid. Preferably the total length of the sense nucleotide sequence is at least 10 nt, preferably 15 nt, particularly at least about 50 nt, more particularly at least about 100 nt, especially at least about 150 nt, more especially at least about 200 nt, quite especially at least about 550 nt. It is expected that there is no upper limit to the total length of the sense nucleotide sequence, other than the total length of the target nucleic acid. However for practical reason (such as e.g. stability of the chimeric genes) it is expected that the length of the sense nucleotide sequence should not exceed 5000 nt, particularly should not exceed 2500 nt and could be limited to about 1000 nt.

It will be appreciated that the longer the total length of the sense nucleotide sequence is, the less stringent the requirements for sequence identity between the total sense nucleotide sequence and the corresponding sequence in the target nucleic acid or gene become. Preferably, the total sense nucleotide sequence should have a sequence identity of at least about 75% with the corresponding target sequence, particularly at least about 80%, more particularly at least about 85%, quite particularly about 90%, especially about 95%, more especially about 100%, quite especially be identical to the corresponding part of the target nucleic acid. However, it is preferred that the sense nucleotide sequence always includes a sequence of about 10 consecutive nucleotides, particularly about 20 nt, more particularly about 50 nt, especially about 100 nt, quite especially about 150 nt with 100% sequence identity to the corresponding part of the target nucleic acid. Preferably, for calculating the sequence identity and designing the corresponding sense sequence, the number of gaps should be minimized, particularly for the shorter sense sequences.

As used herein, "sequence identity" with regard to nucleotide sequences (DNA or RNA), refers to the number of positions with identical nucleotides divided by the number of nucleotides in the shorter of the two sequences. The alignment of the two nucleotide sequences is performed by the Wilbur and Lipmann algorithm (Wilbur and Lipmann, 1983) using a window-size of 20 nucleotides, a word length of 4 nucleotides, and a gap penalty of 4. Computer-assisted analysis and interpretation of sequence data, including sequence alignment as described above, can, e.g., be conveniently performed using the programs of the Intelligenetics™ Suite (Intelligenetics Inc., Calif.). Sequences are indicated as "essentially similar" when such sequence have a sequence identity of at least about 75%, particularly at least about 80%, more particularly at least about 85%, quite particularly about 90%, especially about 95%, more especially about 100%, quite especially are identical. It is clear than when RNA sequences are said to be essentially similar or have a certain degree of sequence identity with DNA sequences, thymine (T) in the DNA sequence is considered equal to uracil (U) in the RNA sequence.

It is expected however, that the target-specific nucleotide sequence may also comprise a nucleotide sequence corresponding to the "antisense" nucleotide sequence of the nucleic acid or gene of interest. In other words, a target-specific antisense nucleotide sequence may be essentially similar to the complement of part of an RNA molecule transcribed or produced from the nucleic acid or gene of interest or to the complement of parts of the nucleic acid or gene of interest controlling the production of that transcribed or produced RNA molecule, when read in the same 5' to 3' direction as the transcribed or produced RNA molecule.

The requirements for antisense target-specific nucleotide sequences with regard to length, similarity etc. are expected to be essentially similar as for sense target-specific nucleotide sequences as specified herein.

It will be clear to the person skilled in the art that the unpolyadenylated RNA molecule may comprise more than one target-specific nucleotide sequence and particularly that the unpolyadenylated RNA molecule may comprise sense and antisense target-specific nucleotide sequences wherein the sense and antisense nucleotide sequences are essentially complementary to each other and capable of forming an artificial hairpin structure as described in Waterhouse et al., 1998 or in PCT-application PCT/IB99/00606 (incorporated by reference). The RNA molecule may comprise a spacer nucleotide sequence located between the sense and antisense nucleotide sequence. It is expected that there are no length limits or sequence requirements associated with the spacer region, as long as these parameters do not interfere with the capability of the RNA regions with the sense and antisense nucleotide sequence to form a double stranded RNA. In a preferred embodiment, the spacer region varies in length from 4 to about 200 bp.

As indicated above, introduction of target-specific unpolyadenylated RNA into the nucleus of a plant cell can conveniently be achieved by transcription of a chimeric DNA encoding RNA introduced into the nucleus, preferably stably integrated into the nuclear genome of a plant cell.

In a preferred embodiment of the invention, the target-specific unpolyadenylated RNA may be produced in the nucleus of a plant cell by transcription of a chimeric DNA encoding a first target-specific RNA, which may be further processed by the action of a ribozyme also present, and preferably also encoded by a chimeric gene, in the plant cell to yield a second unpolyadenylated target-specific RNA. It will be clear for the person skilled in the art that the RNA processing need not be subsequently but can occur simultaneously. In a particularly preferred embodiment the ribozyme is a self-splicing ribozyme which is comprised within the generated target specific RNA transcript.

Thus, in a particularly preferred embodiment of the invention, a method is provided for reducing the phenotypic expression of a nucleic acid of interest, which is normally capable of being expressed in a plant cell, the method comprising the step of introducing into the nuclear genome of the plant cell a chimeric DNA to generate a transgenic plant cell, the chimeric DNA comprising the following operably linked parts:
(a) a plant-expressible promoter region;
(b) a target-specific DNA region;
(c) a DNA region encoding a self-splicing ribozyme; and
(d) a DNA region involved in 3' end formation and polyadenylation wherein the chimeric DNA when transcribed produces a first RNA molecule comprising a target specific nucleotide sequence and a self-splicing ribozyme, which when cleaved by autocatalysis produces a second RNA molecule comprising a target specific nucleotide sequence wherein the 3' end of the first RNA molecule comprising the polyadenylation site has been removed.

The method may optionally further comprise the step of regenerating a the transgenic plant cell into a transgenic plant.

As used herein, "a ribozyme" is a catalytic RNA molecule that has the intrinsic ability to break and form covalent bonds in ribonucleic acids at specific sites in the absence of a cofactor other than a divalent cation.

As used herein a "self-splicing ribozyme" or "self-cleaving ribozyme" is a ribozyme capable of autocatalysis at a specific site within that ribozyme. Preferred self-splicing ribozymes are self-splicing ribozymes with a so-called hammerhead structure. However, it is expected that self-cleaving ribozymes with another conformation such as the hairpin self-cleaving structures encountered in the minus strand of replication intermediates of e.g. the nepoviruses can also be used to the same effect.

Particularly preferred self-splicing ribozymes are those involved in the replication of small circular plant pathogenic RNAs, such as but not limited to the self-splicing ribozyme from avocado sunblotch viroid, peach latent mosaic viroid, Chrysanthemum chlorotic mottle viroid, carnation stunt associated viroid, Newt satellite 2 transcript, *Neurospora* VS RNA, barley yellow dwarf virus satellite RNA, arabis mosaic virus satellite RNA, chicory yellow mottle virus satellite RNA S1, lucerne transient streak virus satellite RNA, tobacco ringspot virus satellite RNA, subterranean clover mottle virus satellite RNA, solanum nodiflorum mottle virus satellite RNA, velvet tobacco mottle virus satellite RNAvSCMoV or Cherry small circular viroid-like RNAcscRNA1. Table 1 lists different variant ribozymes suitable for the invention, as well as a reference to their nucleotide sequence.

The DNA regions encoding self-splicing ribozymes may be cDNA copies of part of the mentioned plant pathogenic RNAs comprising the ribozyme, or may be synthetic DNA. Also comprised are variants such as mutants including substitutions, deletions or insertions of nucleotides within the ribozyme nucleotide sequence in such a way that the autocatalytic capacity of the ribozymes is not substantially altered.

Preferably, the DNA region encoding the self-splicing ribozyme is located immediately upstream of the DNA region encoding the 3' end formation and polyadenylation signal. However, having read the specification, the person skilled in the art will immediately realize that the DNA region encoding the self-splicing ribozyme may be comprised within the chimeric gene encoding the unpolyadenylated RNA at other locations, provided that a sufficiently large second RNA comprising a target-specific nucleotide wherein the polyadenylation site is removed may be generated.

TABLE 1

Different self-cleaving ribozymes

| RNA species | Reference | | Accession Nr | (+) strand | (−) strand |
|---|---|---|---|---|---|
| Avocado sunblotch viroid | Symons | 1981 Nucleic Acids Res. 9 6527-6537 | J02020 | hammerhead | hammerhead |
| Avocado sunblotch viroid variant C-10 | Rakowski and Symons | 1989 Virology 173 352-356 | M31100 | hammerhead | hammerhead |
| Avocado sunblotch viroid variant B-1 | Rakowski and Symons | 1989 Virology 173 352-356 | M31086 | hammerhead | hammerhead |
| Avocado sunblotch viroid variant A-2 | Rakowski and Symons | 1989 Virology 173 352-356 | M31085 | hammerhead | hammerhead |
| Avocado sunblotch viroid variant B-2 | Rakowski and Symons | 1989 Virology 173 352-356 | M31087 | hammerhead | hammerhead |
| Avocado sunblotch viroid variant C-2 | Rakowski and Symons | 1989 Virology 173 352-356 | M31092 | hammerhead | hammerhead |
| Avocado sunblotch viroid variant B-3 | Rakowski and Symons | 1989 Virology 173 352-356 | M31088 | hammerhead | hammerhead |
| Avocado sunblotch viroid variant C-3 | Rakowski and Symons | 1989 Virology 173 352-356 | M31093 | hammerhead | hammerhead |
| Avocado sunblotch viroid variant B-4 | Rakowski and Symons | 1989 Virology 173 352-356 | M31089 | hammerhead | hammerhead |
| Avocado sunblotch viroid variant C-4 | Rakowski and Symons | 1989 Virology 173 352-356 | M31094 | hammerhead | hammerhead |
| Avocado sunblotch viroid variant B-5 | Rakowski and Symons | 1989 Virology 173 352-356 | M31090 | hammerhead | hammerhead |
| Avocado sunblotch viroid variant C-5 | Rakowski and Symons | 1989 Virology 173 352-356 | M31095 | hammerhead | hammerhead |
| Avocado sunblotch viroid variant B-6 | Rakowski and Symons | 1989 Virology 173 352-356 | M31091 | hammerhead | hammerhead |
| Avocado sunblotch viroid variant C-6 | Rakowski and Symons | 1989 Virology 173 352-356 | M31096 | hammerhead | hammerhead |
| Avocado sunblotch viroid variant C-7 | Rakowski and Symons | 1989 Virology 173 352-356 | M31097 | hammerhead | hammerhead |
| Avocado sunblotch viroid variant C-8 | Rakowski and Symons | 1989 Virology 173 352-356 | M31098 | hammerhead | hammerhead |
| Avocado sunblotch viroid variant C-9 | Rakowski and Symons | 1989 Virology 173 352-356 | M31099 | hammerhead | hammerhead |
| Avocado sunblotch viroid ASBVd-B | Semancik and Szychowski | 1994 J. Gen Virol. 75 1543-1549 | S74687 | hammerhead | hammerhead |
| Avocado sunblotch viroid ASBVd-V | Semancik and Szychowski | 1994 J. Gen Virol. 75 1543-1549 | S73861 | hammerhead | hammerhead |

TABLE 1-continued

Different self-cleaving ribozymes

| RNA species | Reference | | Accession Nr | (+) strand | (−) strand |
|---|---|---|---|---|---|
| Peach latent mosaic viroid PLMVd.1 | Hernandez and Flores | 1992 Proc. Natl. Acad. Sci. 89 3711-3715 | M83545 | hammerhead | hammerhead |
| Peach latent mosaic viroid PLMVd.2 | Hernandez and Flores | 1992 Proc. Natl. Acad. Sci. 89 3711-3715 | | hammerhead | hammerhead |
| Peach latent mosaic viroid Peach-Italy | Schamloul et al. | 1995 Acta Hortic. 386 522-530 | | hammerhead | hammerhead |
| Peach latent mosaic viroid Cherry-Canada | Hadini et al. | 1997 Plant Dis. 81, 154-158 | | hammerhead | hammerhead |
| Peach latent mosaic viroid variant gds2 | Ambros et al. | 1998 J. Virol. 72 7397-7406 | AJ005294 | hammerhead | hammerhead |
| Peach latent mosaic viroid variant gds21 | Ambros et al. | 1998 J. Virol. 72 7397-7406 | AJ005295 | hammerhead | hammerhead |
| Peach latent mosaic viroid variant gds15 | Ambros et al. | 1998 J. Virol. 72 7397-7406 | AJ005296 | hammerhead | hammerhead |
| Peach latent mosaic viroid variant gds23 | Ambros et al. | 1998 J. Virol. 72 7397-7406 | AJ005297 | hammerhead | hammerhead |
| Peach latent mosaic viroid variant gds18 | Ambros et al. | 1998 J. Virol. 72 7397-7406 | AJ005298 | hammerhead | hammerhead |
| Peach latent mosaic viroid variant gds1 | Ambros et al. | 1998 J. Virol. 72 7397-7406 | AJ005299 | hammerhead | hammerhead |
| Peach latent mosaic viroid variant gds3 | Ambros et al. | 1998 J. Virol. 72 7397-7406 | AJ005300 | hammerhead | hammerhead |
| Peach latent mosaic viroid variant gds19 | Ambros et al. | 1998 J. Virol. 72 7397-7406 | AJ005301 | hammerhead | hammerhead |
| Peach latent mosaic viroid variant gds13 | Ambros et al. | 1998 J. Virol. 72 7397-7406 | AJ005302 | hammerhead | hammerhead |
| Peach latent mosaic viroid variant gds6 | Ambros et al. | 1998 J. Virol. 72 7397-7406 | AJ005303 | hammerhead | hammerhead |
| Peach latent mosaic viroid variant gds16 | Ambros et al. | 1998 J. Virol. 72 7397-7406 | AJ005304 | hammerhead | hammerhead |
| Peach latent mosaic viroid variant esc8 | Ambros et al. | 1998 J. Virol. 72 7397-7406 | AJ005305 | hammerhead | hammerhead |
| Peach latent mosaic viroid variant esc16 | Ambros et al. | 1998 J. Virol. 72 7397-7406 | AJ005306 | hammerhead | hammerhead |
| Peach latent mosaic viroid variant esc5 | Ambros et al. | 1998 J. Virol. 72 7397-7406 | AJ005307 | hammerhead | hammerhead |
| Peach latent mosaic viroid variant esc12 | Ambros et al. | 1998 J. Virol. 72 7397-7406 | AJ005308 | hammerhead | hammerhead |
| Peach latent mosaic viroid variant esc 10 | Ambros et al. | 1998 J. Virol. 72 7397-7406 | AJ005309 | hammerhead | hammerhead |
| Peach latent mosaic viroid variant esc 14 | Ambros et al. | 1998 J. Virol. 72 7397-7406 | AJ005310 | hammerhead | hammerhead |
| Peach latent mosaic viroid variant ls4b | Ambros et al. | 1998 J. Virol. 72 7397-7406 | AJ005311 | hammerhead | hammerhead |
| Peach latent mosaic viroid variant ls16b | Ambros et al. | 1998 J. Virol. 72 7397-7406 | AJ005312 | hammerhead | hammerhead |
| Peach latent mosaic viroid variant ls17b | Ambros et al. | 1998 J. Virol. 72 7397-7406 | AJ005313 | hammerhead | hammerhead |
| Peach latent mosaic viroid variant ls1 | Ambros et al. | 1998 J. Virol. 72 7397-7406 | AJ005314 | hammerhead | hammerhead |
| Peach latent mosaic viroid variant ls18b | Ambros et al. | 1998 J. Virol. 72 7397-7406 | AJ005315 | hammerhead | hammerhead |
| Peach latent mosaic viroid variant ls11 | Ambros et al. | 1998 J. Virol. 72 7397-7406 | AJ005316 | hammerhead | hammerhead |
| Peach latent mosaic viroid variant ls8 | Ambros et al. | 1998 J. Virol. 72 7397-7406 | AJ005317 | hammerhead | hammerhead |
| Peach latent mosaic viroid variant ls19b | Ambros et al. | 1998 J. Virol. 72 7397-7406 | AJ005318 | hammerhead | hammerhead |
| Peach latent mosaic viroid variant ls5b | Ambros et al. | 1998 J. Virol. 72 7397-7406 | AJ005319 | hammerhead | hammerhead |
| Peach latent mosaic viroid variant ls11b | Ambros et al. | 1998 J. Virol. 72 7397-7406 | AJ005320 | hammerhead | hammerhead |
| Peach latent mosaic viroid variant ls6b | Ambros et al. | 1998 J. Virol. 72 7397-7406 | AJ005321 | hammerhead | hammerhead |
| Peach latent mosaic viroid variant ls14b | Ambros et al. | 1998 J. Virol. 72 7397-7406 | AJ005322 | hammerhead | hammerhead |
| Crysanthemum chlorotic mottle viroid | Navarro and Flores | 1997 Proc. Natl. Acad. Sci. 94 11262-11267 | Y14700 | hammerhead | hammerhead |
| Barley yellow dwarf virus satellite RNA | Miller et al. | 1991 Virology 183 711-720 | M63666 | hammerhead | hammerhead |
| Arabis mosaic virus satellite RNA | Kaper et al. | 1988 Biochem. Biophys. Res. Com. 154 318-325 | M21212 | hammerhead | hairpin |
| Chicory yellow mottle virus satellite RNA S1 | Rubino et al. | 1990 J. Gen Virol. 71 1897-1903 | D00721 | hammerhead | hairpin |
| Lucerne transient streak virus satellite RNA LTSV-N | Keese et al. | 1983 FEBS Lett. 159 185-190 | X01985 | hammerhead | hammerhead |
| Lucerne transient streak virus satellite RNA LTSV-A | Keese et al. | 1983 FEBS Lett. 159 185-190 | X01984 | hammerhead | hammerhead |
| Lucerne transient streak virus satellite RNA LTSV-C | Abouhaidar and Paliwal | 1988 J. Gen. Virology 69 2369-2373 | D00341 | hammerhead | hammerhead |
| Tobacco ringspot virus satellite RNA.1 | Buzayan et al. | 1986 Virology 151, 186-199 | M14879 | hammerhead | hairpin |
| Tobacco ringspot virus satellite RNA.2 | Buzayan et al. | 1987 Virology 160, 95-99 | M17439 | hammerhead | hairpin |
| Subterraneanclover mottle virus satellite RNA.1 | Davies et al. | 1990 Virology 177, 216-224 | M33001 | hammerhead | |
| Subterraneanclover mottle virus satellite RNA.2 | Davies et al. | 1990 Virology 177, 216-224 | M33000 | hammerhead | |
| Solanum nodiflorum mottle virus RNA | Haseloff and Symons | 1982 Nucleic Acids Res. 10 3681-3691 | J02386 | hammerhead | |
| Velvet tobacco mottle virus circular viroid-like RNA-1 | Haseloff and Symons | 1982 Nucleic Acids Res. 10 3681-3691 | | hammerhead | |
| Velvet tobacco mottle virus circular viroid-like RNA-2 | Haseloff and Symons | 1982 Nucleic Acids Res. 10 3681-3691 | J02439 | hammerhead | |
| Cherry small circular viroid-like RNA | Di Serio et al. | 1997 J. Virol. 71 6603-6610 | Y12833 | mod. hammerhead | mod. hammerhead |
| Carnation small viroid-like RNA-1 | Hernandez et al. | 1992 Nucleic Acids Res. 20 6323-6329 | X68034 | hammerhead | hammerhead |
| Carnation small viroid-like RNA-2 | Hernandez et al. | 1992 Nucleic Acids Res. 20 6323-6329 | | hammerhead | hammerhead |
| Notophtalmus viridescens (Newt) satellite 2 transcript | Epstein et al. | 1986 J. Cell. Biol. 103 1137-1144 | X04478 | hammerhead | |
| Neurospora VS RNA | Saville and Collins | 1990 Cell 61 685-696 | M32974 | VS RNA selfcleavage | |
| Schistosome satellite DNA | Ferbeyre et al. | 1998 Mol. Cell. Biol. 18 3880-3888 | AF036739 | | |

The use of ribozymes in transgenic organisms to generate RNA molecules with 5' and or 3' termini of interest has been documented in the art. Rubio et al. 1999, describe broad-spectrum protection against Tombusviruses elicited by defective interfering (DI) RNAs in transgenic plants. To produce RNAs with authentic 5' and 3' termini identical to those of native DI RNA, the DI RNA sequence transcribed from a DNA cassette was flanked by ribozymes. Transgenic *Nicotiana benthamiana* plants were better protected than non-transgenic plants against infection by tomato bushy stunt virus and related tombusviruses. DI RNAs interfere drastically with virus accumulation through effective competition with the parental virus for transacting factors required for replication. Egli and Braus, 1994 describe uncoupling of mRNA 3' cleavage and polyadenylation by expression of a hammerhead ribozyme in yeast. Eckner et al. 1991 described that test gene transcripts which could obtain a mature histone 3' end by the RNA cleaving activity of a cis-acting ribozyme, thus circumventing the cellular 3' end processing machinery were found to be transport deficient and accumulated in the nuclear compartment. However, these documents in the art are not related to methods for inhibiting phenotypic expression by homology dependent gene-silencing, particularly by PTGS.

A particularly preferred self-splicing ribozyme is the ribozyme comprised with the Barley yellow dwarf virus (BYDV) satellite RNA, quite particularly the satellite RNA found in BYDV isolates of the RPV serotype.

It has been found that reduction of the phenotypic expression of the nucleic acid of interest using a chimeric gene according to the invention was most efficient using a cDNA copy of the ribozyme comprised within the minus strand of BYDV satellite RNA. Therefore, ribozymes which show an autocatalytic activity similar to the autocatalytic activity of the ribozyme comprised within the minus strand of BYDV satellite RNA are especially suited for the methods of the invention. Autocatalytic activity of ribozymes can be compared with the autocatalytic activity of the (−) strand of BYDV satellite RNA as described by Miller et al. 1991.

The ribozyme motif within the (−) strand of BYDV satellite RNA has been identified as the nucleotide sequence of SEQ ID No 1 from the nucleotide at position 194 to the nucleotide at position 236. The ribozyme motif within the (+) strand of BYDV satellite RNA has been identified as the nucleotide sequence of SEQ ID No 2 from the nucleotide at position 310 to the nucleotide at position 322 followed by the nucleotide sequence of SEQ ID No. 2 from the nucleotide at position 1 to the nucleotide at position 89.

It goes without saying that more than one DNA region encoding a ribozyme may be comprised within the chimeric gene. These ribozymes may be clustered, e.g. they may all be located the region immediately proceeding DNA region encoding the '3 end formation and polyadenylation signal.

However, it is expected that more than one DNA region encoding a ribozyme may be comprised within the chimeric gene in such a way that upon self-cleavage more than one unpolyadenylated RNA molecules each comprising a target-specific nucleotide sequence is generated. Such a chimeric DNA could thus comprise:

a plant expressible promoter a first target-specific DNA region a DNA region encoding a first self-splicing ribozyme a second target-specific DNA region a DNA region encoding a second self-splicing ribozyme a DNA region encoding a 3' end formation and polyadenylation signal.

The first and second self-splicing ribozyme may be identical, essentially similar or different. Likewise, the first and second target-specific DNA region encoding the RNA with a target-specific nucleotide sequence may be identical, essentially similar or different.

For practical reasons, it is thought that the number of DNA regions encoding a ribozyme within a single chimeric gene should not exceed five.

In a preferred embodiment, the nucleic acid of interest, whose phenotypic expression is targeted to be reduced, is a gene incorporated in the genome of a eukaryotic cell, particularly a plant cell. It will be appreciated that the means and methods of the invention can be used for the reduction of phenotypic expression of a gene which belongs to the genome of the cell as naturally occurring, (an endogenous gene), as well as for the reduction of phenotypic expression of a gene which does not belong to the genome of the cell as naturally occurring, but has been introduced in that cell (a transgene). The transgene can be introduced stably or transiently, and can be integrated into the nuclear genome of the cell, or be present on a replicating vector, such as a viral vector.

In another preferred embodiment, the nucleic acid of interest, whose phenotypic expression is targeted to be reduced is a viral nucleic acid, particularly a viral RNA molecule, capable of infecting a eukaryotic cell, particularly a plant cell. In this case, the phenotype to be reduced is the replication of the virus, and ultimately, the disease symptoms caused by the infecting virus.

For the purpose of the invention, the term "plant-expressible promoter" means a promoter which is capable of driving transcription in a plant cell. This includes any promoter of plant origin, but also any promoter of non-plant origin which is capable of directing transcription in a plant cell. A whole range of plant expressible promoters, is available to direct the transcription of the chimeric genes of the invention. These include, but are not limited to strong promoters such as CaMV35S promoters (e.g., Harpster et al., 1988). In the light of the existence of variant forms of the CaMV35S promoter, as known by the skilled artisan, the object of the invention can equally be achieved by employing these alternative CaMV35S promoters and variants. It is also clear that other plant-expressible promoters, particularly constitutive promoters, such as the opine synthase promoters of the *Agrobacterium* Ti- or Ri-plasmids, particularly a nopaline synthase promoter, or subterranean clover virus promoters can be used to obtain similar effects. Also contemplated by the invention are chimeric genes to reduce the phenotypic expression of a nucleic acid in a cell, which are under the control of single subunit bacteriophage RNA polymerase specific promoters, such as a T7 or a T3 specific promoter, provided that the host cells also comprise the corresponding RNA polymerase in an active form.

It is a further object of the invention, to provide methods for reducing the phenotypic expression of a nucleic acid in specific cells, particularly specific plant cells by placing the chimeric genes of the invention under control of tissue-specific or organ-specific promoters. Such tissue-specific or organ-specific promoters are well known in the art and include but are not limited to seed-specific promoters (e.g., WO89/03887), organ-primordia specific promoters (An et al., 1996), stem-specific promoters (Keller et al., 1988), leaf specific promoters (Hudspeth et al., 1989), mesophyl-specific promoters (such as the light-inducible Rubisco promoters), root-specific promoters (Keller et al., 1989), tuber-specific promoters (Keil et al., 1989), vascular tissue specific promoters (Peleman et al., 1989), stamen-selective promoters (WO 89/10396, WO 92/13956), dehiscence zone specific promoters (WO 97/13865) and the like.

In another embodiment of the invention, the expression of a chimeric gene to reduce the phenotypic expression of a target nucleic acid can be controlled at will by the application of an appropriate chemical inducer, by operably linking the transcribed DNA region of the chimeric genes of the invention to a promoter whose expression is induced by a chemical compound, such as the promoter of the gene disclosed in European Patent publication ("EP") 0332104, or the promoter of the gene disclosed in WO 90/08826.

It will be clear to the person skilled in the art that the same effect in reducing the phenotypic expression of a nucleic acid in a plant cell may be achieved using a trans-splicing ribozyme to remove at least the polyadenylation site from the RNA transcript of a chimeric gene comprising a plant expressible promoter, a target-specific DNA region and a DNA region encoding a 3' end termination and polyadenylation signal to generate unpolyadenylated RNA comprising a target-specific nucleotide sequence.

As used herein "a trans-splicing ribozyme" is an RNA molecule capable of catalyzing the breakage or formation of a covalent bond within another RNA molecule at a specific site.

The trans-splicing ribozyme should be chosen or designed in such a way that it recognizes a specific site preceding, preferably immediately preceding the polyadenylation signal of the RNA transcript comprising a target-specific nucleotide sequence. Methods to design such trans-splicing ribozyme with endoribonuclease activity are known in the art (see e.g. Haselhoff and Gerlach, 1988, WO 89/05852)

The DNA region encoding a trans-splicing ribozyme may be comprised within the chimeric gene encoding the target-specific RNA. Upon transcription of the chimeric gene an RNA molecule comprising the trans-splicing ribozyme and the target-specific nucleotide sequence may then generated, wherein the trans-splicing ribozyme is capable of cleaving a specific site preceding the polyadenylation site of another similar RNA molecule, to generate unpolyadenylated target-specific RNA molecules.

The trans-splicing ribozyme may also be provided by expression of another chimeric gene encoding an RNA molecule comprising the trans-splicing ribozyme in the same plant cell, according to methods and means available in the art (see e.g. Vaish et al. 1998; Bramlage et al. 1998).

Alternative methods may exist to provide unpolyadenylated target-specific RNA to the nucleus of a plant cell. Such methods include e.g. transcription of a chimeric gene, integrated in the nuclear genome of a plant cell comprising a target-specific DNA region, by an DNA-dependent RNA polymerase different from RNA polymerase II, such that RNA transcripts are generated independent from the normal processing mRNA machinery (including intron-splicing, capping and polyadenylation). This can be achieved e.g. by operably linking the target-specific DNA region to a promoter region, recognized by a single subunit RNA polymerase from a bacteriophage, such as but not limited to the T7 polymerase, and a DNA region comprising a terminator for such a polymerase. In this case, the plant cell needs to be provided with a chimeric gene encoding the corresponding RNA polymerase. Providing unpolyadenylated target-specific RNA to the nucleus of a plant cell can also be achieved e.g. by operably linking the target-specific DNA region to a promoter region, recognized by a eukaryotic RNA polymerase I or III, and a DNA region comprising a terminator for such a polymerase. The means and methods for constructing such chimeric genes and plant cells are described in detail in WO 97/49814 (incorporated by reference). Another alternative to provide unpolyadenylated target-specific RNA to the nucleus of a plant cell may include transcription of a chimeric gene comprising a target-specific DNA region operably linked to a plant-expressible promoter and linked to a DNA region comprising a 3' end formation signal but not a polyadenylation signal.

Although not intending to limit the invention to a specific mode of action, it is expected that the trigger of the homology-dependent gene-silencing mechanisms of the cell, particularly the co-suppression mechanism, is the accumulation of target-specific RNA into the nucleus of that cell. Providing unpolyadenylated RNA to the nucleus of the cell may be one mechanism of causing accumulation of target-specific RNA in a nucleus of a cell, but other aberrations such as the absence of a cap-structure or the presence of persistent introns etc. may constitute alternative ways to cause the accumulation of target-specific RNA in the nucleus of a cell.

Moreover, it is expected that other aberrations in the target-specific RNA molecules in addition to the absence of the polyA tail, including the absence of a cap-structure, or the presence of persistent introns or the presence of abnormal secondary structures, particularly the presence of giant hairpin structures, may have a cumulative effect on the inhibition of the normal transit of the RNA from the nucleus to the cytoplasm and hence have a cumulative or synergystic effect on the reduction of the phenotypic expression of a nucleic acid of interest.

The recombinant DNA comprising the chimeric gene to reduce the phenotypic expression of a nucleic acid of interest in a host cell, may be accompanied by a chimeric marker gene, particularly when the stable integration of the transgene in the genome of the host cell is envisioned. The chimeric marker gene can comprise a marker DNA that is operably linked at its 5' end to a promoter, functioning in the host cell of interest, particularly a plant-expressible promoter, preferably a constitutive promoter, such as the CaMV 35S promoter, or a light inducible promoter such as the promoter of the gene encoding the small subunit of Rubisco; and operably linked at its 3' end to suitable plant transcription 3' end formation and polyadenylation signals. It is expected that the choice of the marker DNA is not critical, and any suitable marker DNA can be used. For example, a marker DNA can encode a protein that provides a distinguishable colour to the transformed plant cell, such as the A1 gene (Meyer et al., 1987), can provide herbicide resistance to the transformed plant cell, such as the bar gene, encoding resistance to phosphinothricin (EP 0,242,246), or can provide antibiotic resistance to the transformed cells, such as the aac(6') gene, encoding resistance to gentamycin (WO94/01560).

A recombinant DNA comprising a chimeric gene to reduce the phenotypic expression of a gene of interest, can be stably incorporated in the nuclear genome of a cell of a plant. Gene transfer can be carried out with a vector that is a disarmed Ti-plasmid, comprising a chimeric gene of the invention, and carried by *Agrobacterium*. This transformation can be carried out using the procedures described, for example, in EP 0 116 718.

Alternatively, any type of vector can be used to transform the plant cell, applying methods such as direct gene transfer (as described, for example, in EP 0 233 247), pollen-mediated transformation (as described, for example, in EP 0 270 356, WO85/01856 and U.S. Pat. No. 4,684,611), plant RNA virus-mediated transformation (as described, for example, in EP 0 067 553 and U.S. Pat. No. 4,407,956), liposome-mediated transformation (as described, for example, in U.S. Pat. No. 4,536,475), and the like.

Other methods, such as microprojectile bombardment as described for corn by Fromm et al. (1990) and Gordon-Kamm et al. (1990), are suitable as well. Cells of monocotyledonous plants, such as the major cereals, can also be transformed using wounded and/or enzyme-degraded compact embryogenic tissue capable of forming compact embryogenic callus, or wounded and/or degraded immature embryos as described in WO92/09696. The resulting transformed plant cell can then be used to regenerate a transformed plant in a conventional manner.

The obtained transformed plant can be used in a conventional breeding scheme to produce more transformed plants with the same characteristics or to introduce the chimeric gene for reduction of the phenotypic expression of a nucleic acid of interest of the invention in other varieties of the same or related plant species, or in hybrid plants. Seeds obtained from the transformed plants contain the chimeric genes of the invention as a stable genomic insert.

The means and methods of the invention can also be used for the reduction of gene expression by co-suppression in eukaryotic cells and organisms.

In one embodiment the invention provides a method for reducing the phenotypic expression of a nucleic acid of interest, which is normally capable of being expressed in a eukaryotic cell, comprising the step of providing unpolyadenylated RNA comprising a target specific sense nucleotide sequence of at least 10 consecutive nucleotides with at least about 70% sequence identity to about 100% sequence identity to the nucleotide sequence of the nucleic acid of interest, to the nucleus of the eukaryotic cell.

In another embodiment, a method is provided for reducing the phenotypic expression of a nucleic acid of interest, which is normally capable of being expressed in a eukaryotic cell, comprising the step of introducing into the nuclear genome of the eukaryotic cell a chimeric DNA to generate a transgenic plant cell, DNA comprising the following operably linked parts:
  (e) a promoter region functional in the eukaryotic cell;
  (f) a target-specific DNA region comprising nucleotide sequence of at least 10 consecutive nucleotides with at least about 70% sequence identity to about 100% sequence identity to the nucleotide sequence of the nucleic acid of interest;
  (g) a DNA region encoding a self-splicing ribozyme; and
  (h) a DNA region involved in 3' end formation and polyadenylation wherein the chimeric DNA when transcribed produces a first RNA molecule comprising a target specific nucleotide sequence and a self-splicing ribozyme, which when cleaved by autocatalysis produces a second RNA molecule comprising a target specific nucleotide sequence wherein the 3' end of the first RNA molecule comprising the polyadenylation site has been removed.

Different preferred embodiments and definitions described in connection with the reduction of gene expression by homology dependent gene silencing in plant cells and plants also apply mutatis mutandis to the means and methods described for reduction of gene expression by co-suppression in eukaryotic cells and organisms. As used herein "eukaryotic cells" comprise plant cells, animal cells and human cells and cells from yeasts and fungi as well as cultures of such cells.

It is a further object of the invention to provide eukaryotic cells, preferably plant cells and organisms (preferably plants) comprising the chimeric genes for the reduction of the phenotypic expression of a target nucleic acid as described in the invention.

The methods and means of the invention can thus be used to reduce phenotypic expression of a nucleic acid in a eukaryotic cell or organism, particularly a plant cell or plant, for obtaining shatter resistance (WO 97/13865), for obtaining modified flower colour patterns (EP 522 880, U.S. Pat. No. 5,231,020), for obtaining nematode resistant plants (WO 92/21757, WO 93/10251, WO 94/17194), for delaying fruit ripening (WO 91/16440, WO 91/05865, WO 91/16426, WO 92/17596, WO 93/07275, WO 92/04456, U.S. Pat. No. 5,545,366), for obtaining male sterility (WO 94/29465, WO89/10396, WO 92/18625), for reducing the presence of unwanted (secondary) metabolites in organisms, such as glucosinolates (WO97/16559) or chlorophyll content (EP 779 364) in plants, for modifying the profile of metabolites synthesized in a eukaryotic cell or organisms by metabolic engineering e.g. by reducing the expression of particular genes involved in carbohydrate metabolism (WO 92/11375, WO 92/11376, U.S. Pat. No. 5,365,016, WO 95/07355) or lipid biosynthesis (WO 94/18337, U.S. Pat. No. 5,530,192), for delaying senescence (WO 95/07993), for altering lignification in plants (WO 93/05159, WO 93/05160), for altering the fibre quality in cotton (U.S. Pat. No. 5,597,718), for increasing bruising resistance in potatoes by reducing polyphenoloxidase (WO 94/03607), etc.

The methods of the invention will lead to better results and/or higher efficiencies when compared to the methods using conventional sense or antisense nucleotide sequences and it is believed that other sequence-specific mechanisms regulating the phenotypic expression of target nucleic acids might be involved and/or triggered by the presence of the double-stranded RNA molecules described in this specification.

A particular application for reduction of the phenotypic expression of a transgene in a plant cell, inter alia, by antisense or sense methods, has been described for the restoration of male fertility, the latter being obtained by introduction of a transgene comprising a male sterility DNA (WO 94/09143, WO 91/02069). The nucleic acid of interest is specifically the male sterility DNA. Again, the processes and products described in this invention can be applied to these methods in order to arrive at a more efficient restoration of male fertility.

It will be appreciated that the methods and means described in the specification can also be applied in High Throughput Screening (HTS) methods, for the identification or confirmation of phenotypes associated with the expression of a nucleic acid sequence with hitherto unidentified function in a eukaryotic cell, particularly in a plant cell.

Such a method comprises the steps of:
  1. Selecting a target sequence within the nucleic acid sequence of interest with unidentified or non-confirmed function/phenotype when expressed. Preferably, if the nucleic acid has putative open reading frames, the target sequence should comprise at least part of one of these open reading frames. The length of the target nucleotide sequence may vary from about 10 nucleotides up to a length equaling the length (in nucleotides) of the nucleic acid of interest with unidentified function.
  2. Introducing a chimeric DNA into the nucleus of a suitable host cell, comprising the nucleic acid of interest, wherein the chimeric DNA comprises a promoter region suitable for expression in the host cell, a DNA region encoding the target-specific nucleotide sequence, and a DNA region encoding a self-splicing ribozyme located immediately upstream of a DNA region involved in 3' end formation and polyadenylation.
  3. Observing the phenotype by a suitable method. Depending on the phenotype expected, it may be sufficient to observe or measure the phenotype in a single cell, but it may also be required to culture the cells to obtain an (organized) multicellular level, or even to regenerate a transgenic organism, particularly a transgenic plant.

It is also clear that the methods and means of the invention are suited for the reduction of the phenotypic expression of a nucleic acid in all plant cells of all plants, whether they are monocotyledonous or dicotyledonous plants, particularly crop plants such as but not limited to corn, rice, wheat, barley, sugarcane, cotton, oilseed rape, soybean, vegetables (including chicory, brassica vegetables, lettuce, tomato), tobacco, potato, sugarbeet but also plants used in horticulture, floriculture or forestry. The means and methods of the invention will be particularly suited for plants which have complex genomes, such as polyploid plants.

It is expected that the chimeric RNA molecules produced by transcription of the chimeric genes described herein, can spread systemically throughout a plant, and thus it is possible to reduce the phenotypic expression of a nucleic acid in cells of a non-transgenic scion of a plant grafted onto a transgenic stock comprising the chimeric genes of the invention (or vice versa) a method which may be important in horticulture, viticulture or in fruit production.

The following non-limiting Examples describe the construction of chimeric genes for the reduction of the phenotypic expression of a nucleic acid of interest in a eukaryotic cell and the use of such genes. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, NY and in Volumes 1 and 2 of Ausubel et al. (1994) *Current Protocols in Molecular Biology, Current Protocols*, USA. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK.

Throughout the description and Examples, reference is made to the following sequences:

SEQ ID No 1: cDNA copy of the (−) strand of BYDV RPV satellite RNA

SEQ ID No 2: cDNA copy of the (+) strand of BYDV RPV satellite RNA

SEQ ID No 3: oligonucleotide for PCR amplification (SatPR1)

SEQ ID No 4: oligonucleotide for PCR amplification (SatPR2)

SEQ ID No 5: oligonucleotide for PCR amplification (SatPR3)

SEQ ID No 6: oligonucleotide for PCR amplification (SatPR4)

The following examples are presented in order to more fully illustrate the preferred embodiments of the invention and should not be construed, however, as limiting the broad scope of the invention.

EXAMPLES

Example 1

Experimental Procedures 1.1 Chimeric DNA Constructs

Ribozyme-Containing Gus Gene Constructs and a Control Construct

The ribozyme sequences used are the plus strand or negative strand self-cleavage sequences of the satellite RNA of the barley yellow dwarf virus (BYDV) RPV serotype, which was isolated in CSIRO Plant Industry (SEQ ID 1 and 2; Miller et al., 1991).

The two ribozyme-containing GUS constructs (pMBW259 and pMBW267) and one control GUS construct (pMBW265) are schematically drawn in FIG. 1. pMBW259 contains two plus strand cleavage sites, while pMBW267 contains the negative strand cleavage site.

To make these constructs, a β-glucuronidase (GUS) gene sequence was modified to contain a NcoI site around the translational start ATG and cloned into pART7 (Gleave, 1992) at the XhoI/EcoRI sites, forming pMBW258. The full-length BYDV-RPV satellite sequence was amplified by PCR using primers SatPR1 (SEQ ID No. 3) and SatPR4 (SEQ ID No. 6), digested with BamHI and cloned into pMBW258 at the BamHI site, and the resulting 35S-GUS-Sat-ocs cassette was excised and cloned into pART27 (Gleave, 1992), forming pMBW265. The same full-length satellite sequence was inserted into the BamHI site of pMBW258 but in the antisense orientation, and the resulting 35S-GUS-asSat-ocs was cloned into pART27 to give rise to pMBW267.

To make pMBW259, the 3' and 5' halfs of the satellite RNA sequences were amplified by PCR using primer pairs SatPR3 (SEQ ID No. 5) and SatPR4 (SEQ ID No. 6), and using SatPR1 (SEQ ID No. 3) and SatPR2 (SEQ ID No 4), respectively. Fusion of the full-length sequence with the 3' half and the 5' half sequences were made through ligation between the EcoRV and HpaI ends of the three PCR fragments. This fusion mimics the natural multimeric forms of the satellite RNA, and therefore maintains the plus strand cleavage property of the native forms. The fusion sequence was cloned into pGEM-3Z (Promega) at the SacI/PstI sites, excised with HindIII/EcoRI, blunted, and inserted into pART7 at the SmaI site, into which the GUS sequence described above was then cloned at the XhoI/EcoRI sites. The resulting 3SS-GUS-Sat-ocs was inserted into pART27 at the NotI site, forming pMBW259.

The Super-Transforming GUS Construct

The BamHI fragment was excised from pIG121 Hm (Hiei et al., 1994) and cloned into pART7. The GUS-nos sequence was then excised by AccI, blunted, and inserted into pBluescript at the HincII site. The 1.3 kb promoter region of a cucurbit phloem protein PP2 gene was excised with NotI/HindIII from a lambda clone CPPI.3 and cloned into the above Bluescript plasmid. The resulting PP2-GUS-nos was excised with NotI/KpnI and inserted into pWBVec2 (Wang et al., 1998), giving rise to pBPPGH (FIG. 1).

1.2 Tobacco Transformation

*Nicotiana tobaccum* cv. W38 was transformed and regenerated into whole plants essentially as described by Ellis et al. 1987. For constructs pMBW259, pMBW265 and pMBW267, 50 mg/L kanamycin was included in the media for selection of transformed tissue. For construct pBPPGH, 25 mg/L hygromycin B was used.

1.3 GUS Assay

GUS gene expression was assayed histochemically or fluorometrically according to Jefferson et al. 1987.

Example 2

GUS Expression in Transgenic Tobacco Transformed with a Single Type of the Gus Constructs Transgenic plants containing pMBW259 and pMBW267 showed very low levels of GUS expression, as judged by lack of, or faint blue, GUS staining. Plants transformed with pMBW265 showed more GUS expression than with pMBW259 and pMBW267, but the level was much lower than plants transformed with pBPPGH. The best pMBW265 lines expressed 13.3% of the GUS activity by an average pBPPGH line.

Example 3

GUS Expression in Super-Transformed Lines Containing pBPPGH and one of the three other constructs of Example 1.

In order to promote silencing of a normal GUS gene by the presence of the ribozyme sequence near the 3' end of the GUS gene transcript, plants containing pMBW259, pMBW265 or pMBW267 and pBPPGH were constructed by re-transformation. Histochemical GUS assays of the super-transformants showed that the pMBW267 background gave substantially higher proportions of transformants than the pMBW259 or the pMBW265 background that showed low levels of GUS expression as indicated by the lack of strong and uniform blue staining. Super-transformants containing pBPPGH and pMBW265 showed the best GUS expression.

Table 2 shows the result of fluorometric GUS (MUG) assay of the super-transformants. The lines (E and F) containing pBPPGH and pMBW267 showed uniformly low GUS expression compared with the other lines. The best GUS expression came from the C lines which contain pBPPGH and pMBW265.

Among the three constructs tested, pMBW265 does not contain the full-length functional ribozyme sequences of the BYDV satellite RNA in a continuous stretch, and is therefore expected to produce mainly poly(A)+RNA. pMBW259 contains two copies of the plus strand ribozyme sequence, and should give rise to RNA that have poly(A) tails removed by ribozyme cleavage. pMBW267 contain the negative strand ribozyme. The negative strand ribozyme was previously shown to be much (at least 10-fold) more efficient than the plus strand ribozyme (Miller et al., 1991), and therefore it is expected that pMBW267 produces poly(A)-RNA more efficiently. Our experiment showed that the super-transformed lines having the pMBW267 background expressed uniformly low levels of GUS activity in comparison with the lines having the pMBW259 or the pMBW265 background. The highest GUS expressing lines were from the pMBW265 background, which does not produce polyA-RNA.

TABLE 2

MUG assay of super-transformed tobacco lines*.

| Super-transformed lines | MUG Readings |
| --- | --- |
| A1 | 10.1 |
| A2 | 15.8 |
| A3 | 30.6 |
| A4 | 47.3 |
| A5 | 0.29 |
| A6 | 10.3 |
| A7 | 5.8 |
| A8 | 13.15 |
| A9 | 7.34 |
| A10 | 9.76 |
| A11 | 17.74 |
| A12 | 34.8 |
| A13 | 4.33 |
| A14 | 3.41 |
| A15 | 11.2 |
| A16 | 2.04 |
| A17 | 13.29 |
| A18 | 14.6 |
| A19 | 0.14 |
| A20 | 17.2 |
| A21 | 9.22 |
| A22 | 17.3 |
| B1 | 9.57 |
| B2 | 44.7 |
| B3 | 17.7 |
| B4 | 1.25 |
| B5 | 13.5 |
| B6 | 11.4 |
| B7 | 6.28 |
| B8 | 24.8 |
| B9 | 16.3 |
| B10 | 9.72 |
| B11 | 3.71 |
| B12 | 0.08 |
| B13 | 20.6 |
| B14 | 11.9 |
| B15 | 3.11 |
| B16 | 8.25 |
| B17 | 4.12 |
| B18 | 6.04 |
| C1 | 8.84 |
| C2 | 16.9 |
| C3 | 17.9 |
| C4 | 22.8 |
| C5 | 11.7 |
| C6 | 14.5 |
| C7 | 44.0 |
| C8 | 19.0 |
| C9 | 29.8 |
| C10 | 32.1 |
| C11 | 37.1 |
| C12 | 2.51 |
| C13 | 14.5 |
| C14 | 25.8 |
| C15 | 7.20 |
| C16 | 30.2 |
| C17 | 9.70 |
| C18 | 13.4 |
| C19 | 19.3 |
| C20 | 17.0 |
| D1 | 6.01 |
| D2 | 12.9 |
| D3 | 0.19 |
| D4 | 7.88 |
| D5 | 1.24 |
| D6 | 0.44 |
| D7 | 14.1 |
| D8 | 0.91 |
| D9 | 5.49 |
| D10 | 1.30 |
| D11 | 15.1 |
| D12 | 6.63 |
| D13 | 12.2 |
| D14 | 15.8 |
| D15 | 1.32 |
| D16 | 2.29 |
| D17 | 3.59 |
| D18 | 22.1 |
| D19 | 13.0 |
| D20 | 4.37 |
| E1 | 4.32 |
| E2 | 3.15 |
| E3 | 3.56 |
| E4 | 3.31 |
| E5 | 3.68 |
| E6 | 5.02 |
| E7 | 2.63 |
| E8 | 10.27 |
| E9 | 10.81 |

TABLE 2-continued

MUG assay of super-transformed tobacco lines*.

| Super-transformed lines | MUG Readings |
|---|---|
| E10 | 13.1 |
| E11 | 5.10 |
| E12 | 2.86 |
| E13 | 4.00 |
| E14 | 16.8 |
| E15 | 4.02 |
| E16 | 1.29 |
| E17 | 1.78 |
| E18 | 3.57 |
| E19 | 0.43 |
| E20 | 11.8 |
| F1 | 5.73 |
| F2 | 5.10 |
| F3 | 4.16 |
| F4 | 4.69 |
| F5 | 0 |
| F6 | 1.93 |
| F7 | 3.21 |
| F8 | 2.77 |
| F9 | 1.86 |
| F10 | 3.27 |
| F11 | 2.85 |
| F12 | 3.25 |
| F13 | 2.17 |
| F14 | 2.84 |
| F15 | 3.11 |
| F16 | 2.06 |
| F17 | 2.90 |
| F18 | 3.75 |
| F19 | 4.16 |
| F20 | 2.49 |

*A and B, from super-transformation of two independent pMBW259 lines with pBPPGH; C and D, from super-transformation of two independent pMBW265 lines with pBPPGH; E and F, from super-transformation of two independent pMBW267 lines with pBPPGH.

REFERENCES

An et al., 1996 The Plant Cell 8: 15-30
Bramlage et al. 1998 TIBTECH 16, 434-438
Covey et al., 1997 Nature 385:781-782
Eckner et al. 1991 EMBO J. 10: 3513-3522
Egli and Braus, 1994 J. Biol. Chem. 1994 269: 27378-27383
Ellis et al. 1987 EMBO Journal, 6: 11-16
Fromm et al., 1990 Bio/Technology 8: 833
Gleave, 1992 Plant Mol. Biol. 20: 1203-1207
Gordon-Kamm et al., 1990 The Plant Cell 2: 603
Hamilton et al. 1998 The Plant Journal 15(6): 737-746
Harpster et al., 1988 Mol. Gen. Genet. 212, 182-190
Haselhoff and Gerlach, 1988 Nature 334 585-591
Hiei et al., 1994 Plant Journal 6: 271-282
Hudspeth et al., 1989 Plant Mol Biol 12: 579-589
Jefferson et al., 1987 EMBO J. 6, 3901-3907
Keil et al., 1989 EMBO J. 8: 1323-1330
Keller et al., 1988 EMBO J. 7: 3625-3633
Keller et al., 1989 Genes Devel. 3: 1639-1646
Lee et al. 1997 Plant Journal 12: 1127-1137
Mette et al., 1999 EMBO J 18: 241-248
Metzlaff et al., 1997 Cell 88, 845-854
Miller et al., 1991 Virology 183: 711-720, 1991
Peleman et al., 1989 Gene 84: 359-369
Rubio et al. 1999 J. Virology 73: 5070-5078
Vaish et al. 1998 Nucleic Acids Res. 26: 5237-5242
van Eldik et al. 1998 Nucleic Acids Res. 26: 5176-5181
van Houdt et al., 1997 Plant Journal 12: 379-392
Wang et al., 1998 Acta Horticulturae 461:1-407
Wassenegger and Pelissier, 1998 Plant Mol. Biol. 37 349-362
Waterhouse et al. 1998 Proc. Natl. Acad. Sci USA 95: 13959-13964
Wilbur and Lipmann, 1983 Proc. Nat. Acad. Sci. U.S.A. 80: 726

---

What is claimed is:

1. A method for reducing the phenotypic expression of a nucleic acid of interest, which is normally capable of being expressed in a plant cell, said method comprising:
   providing unpolyadenylated RNA to the nucleus of the cell,
   wherein the unpolyadenylated RNA is produced by transcription of a chimeric DNA comprised within said cell, said chimeric DNA comprising a promoter operably linked to a target-specific DNA region encoding said RNA,
   and wherein the unpolyadenylated RNA comprises a target-specific sense nucleotide sequence, a target-specific antisense nucleotide sequence, and a spacer nucleotide sequence located between said sense and antisense nucleotide sequence,
   wherein the target-specific antisense nucleotide sequence comprises 20 consecutive nucleotides having 100% sequence identity to a sequence complementary to a sequence of 20 consecutive nucleotides of an untranslated region of an RNA molecule transcribed or produced from said nucleic acid of interest, and wherein the target-specific sense nucleotide sequence and the target-specific antisense nucleotide sequence form an artificial hairpin structure with each other.

2. The method of claim 1, wherein the nucleic acid of interest is a gene incorporated in the genome of the cell.

3. The method of claim 1, wherein the nucleic acid of interest is an endogenous gene of the cell.

4. The method of claim 1, wherein the nucleic acid of interest is a transgene.

5. The method of claim 1, wherein the nucleic acid of interest is a viral nucleic acid.

6. The method of claim 1, wherein the target-specific sense nucleotide sequence comprises 20 consecutive nucleotides having 100% sequence identity to a sequence of 20 consecutive nucleotides of the RNA molecule transcribed or produced from the nucleic acid of interest.

7. The method of claim 1, wherein the unpolyadenylated RNA lacks a 5' cap structure.

8. The method of claim 1, wherein the unpolyadenylated RNA comprises a persistent intron that has been modified in its splice sites so as to prevent splicing.

9. The method of claim 1, wherein the chimeric DNA is transcribed to produce a first target-specific RNA, which is processed by the action of a ribozyme to produce the unpolyadenylated RNA.

10. The method of claim 1, wherein the promoter is a promoter recognized by RNA polymerase I.

11. The method of claim 1, wherein the promoter is a promoter recognized by RNA polymerase III.

12. The method of claim 1, wherein the cell is a cultured cell.

13. The method of claim 1, further comprising:
(a) selecting a target sequence of at least 20 consecutive nucleotides within a nucleic acid of interest before
(b) the step of providing unpolyadenylated RNA to the nucleus of the cell, which comprises introducing a chimeric DNA encoding said unpolyadenylated RNA into the nucleus of said cell comprising the nucleic acid of interest, and thereafter (c) observing a phenotype of said cell by a suitable method;
thereby identifying a phenotype associated with the expression of the nucleic acid of interest in the cell.

14. The method of claim 13, wherein the phenotype associated with the expression of the nucleic acid of interest in the cell was previously unidentified.

15. The method of claim 13, wherein the phenotype is observed after culturing of the cells.

16. The method of claim 13, wherein the phenotype is a modified profile of metabolites synthesized in the cell.

17. A chimeric DNA molecule for reducing the phenotypic expression of a nucleic acid of interest that is normally capable of being expressed in a plant cell, said chimeric DNA molecule comprising
a promoter which is operable in the cell, the promoter being operably linked to a sequence encoding an unpolyadenylated RNA capable of reducing expression of the nucleic acid of interest when provided to the nucleus of the cell, the unpolyadenylated RNA comprising:
a target-specific sense nucleotide sequence, a target-specific antisense nucleotide sequence, and a spacer nucleotide sequence located between said sense and antisense nucleotide sequence,
wherein the target-specific antisense nucleotide sequence comprises 20 consecutive nucleotides having 100% sequence identity to a sequence complementary to a sequence of 20 consecutive nucleotides of an untranslated region of an RNA molecule transcribed or produced from said nucleic acid of interest,
wherein the target-specific sense nucleotide sequence and the target-specific antisense nucleotide sequence form an artificial hairpin structure with each other.

18. The chimeric DNA molecule of claim 17, wherein the nucleic acid of interest is a gene incorporated in the genome of the cell.

19. The chimeric DNA molecule of claim 17, wherein the nucleic acid of interest is an endogenous gene of the cell.

20. The chimeric DNA molecule of claim 17, wherein the nucleic acid of interest is a transgene.

21. The chimeric DNA molecule of claim 17, wherein the nucleic acid of interest is a viral nucleic acid.

22. The chimeric DNA molecule of claim 17, wherein the target-specific sense nucleotide sequence comprises 20 consecutive nucleotides having 100% sequence identity to a sequence of 20 consecutive nucleotides of the RNA molecule transcribed or produced from the nucleic acid of interest.

23. The chimeric DNA molecule of claim 17, wherein the promoter is a promoter recognized by RNA polymerase I.

24. The chimeric DNA molecule of claim 17, wherein the promoter is a promoter recognized by RNA polymerase III.

25. A plant or fungal cell, comprising a chimeric DNA molecule comprising:
a promoter that is operable in the cell, the promoter being operably linked to a sequence that encodes an unpolyadenylated RNA capable of reducing a phenotypic expression of a nucleic acid of interest, the unpolyadenylated RNA comprising:
a target-specific sense nucleotide sequence, a target-specific antisense nucleotide sequence, and a spacer nucleotide sequence located between said sense and antisense nucleotide sequence,
wherein the target-specific antisense nucleotide sequence comprises 20 consecutive nucleotides having 100% sequence identity to a sequence complementary to a sequence of 20 consecutive nucleotides of an untranslated region of an RNA molecule transcribed or produced from the nucleic acid of interest which is normally capable of being expressed in the cell,
and wherein the target-specific sense nucleotide sequence and the target-specific antisense nucleotide sequence form an artificial hairpin with each other.

26. The plant cell of claim 25, wherein the cell is a cell in culture.

27. The cell of claim 25, wherein the phenotypic expression of the nucleic acid of interest is reduced relative to a corresponding cell lacking said unpolyadenylated RNA.

28. The cell of claim 25, which has a modified phenotype compared to a corresponding cell lacking said unpolyadenylated RNA.

29. The cell of claim 28, wherein the modified phenotype is a modified profile of metabolites synthesized in the cell.

30. The cell of claim 25, wherein the plant cell is a cell of a monocotyledonous plant.

31. The cell of claim 25, wherein the plant cell is a cell of a dicotyledonous plant.

32. The cell of claim 30, wherein the monocotyledonous plant is corn, rice, wheat, barley, or sugarcane.

33. The cell of claim 31, wherein the dicotyledonous plant is cotton, oilseed rape, soybean, a vegetable, chicory, a *brassica* vegetable, lettuce, tomato, tobacco, potato, or sugarbeet.

34. A transgenic plant, comprising a chimeric DNA molecule comprising
a promoter which is operable in a cell of the plant, the promoter being operably linked to a sequence encoding an unpolyadenylated RNA capable of reducing the expression of a nucleic acid of interest, the unpolyadenylated RNA comprising a target-specific sense nucleotide sequence, a target-specific antisense nucleotide sequence, a spacer nucleotide sequence located between said sense and antisense sequence, wherein the target-specific antisense nucleotide sequence comprises 20 consecutive nucleotides having 100% sequence identity to a sequence complementary to a sequence of 20 consecutive nucleotides of an untranslated region of an RNA molecule transcribed or produced from a nucleic acid of interest which is normally capable of being expressed in the cell, and wherein the target-specific sense nucleotide sequence and the target-specific antisense nucleotide sequence form an artificial hairpin with each other.

35. The transgenic plant of claim 34, wherein the plant is a monocotyledonous plant.

36. The transgenic plant of claim 34, wherein the plant is a dicotyledonous plant.

37. The transgenic plant of claim 35, wherein the monocotyledonous plant is corn, rice, wheat, barley, or sugarcane.

38. The transgenic plant of claim 36, wherein the dicotyledonous plant is cotton, oilseed rape, soybean, a vegetable, chicory, a *brassica* vegetable, lettuce, tomato, tobacco, potato, or sugarbeet.

39. The transgenic plant of claim 34, wherein the plant has a modified phenotype compared to a corresponding plant which is lacking said unpolyadenylated RNA.

40. The transgenic plant of claim 39, wherein the modified phenotype is shatter resistance, a modified pattern of flower color, nematode resistance, delayed fruit ripening, male sterility, a reduced level of a secondary metabolite, reduced expression of a gene involved carbohydrate metabolism or lipid biosynthesis, delayed senescence, altered lignification, altered fibre quality in cotton, or increased bruising resistance in potato by reduced polyphenoloxidase.

41. The method of claim 1 wherein the target-specific antisense nucleotide sequence consists of at least 20 consecutive nucleotides having 100% sequence identity to a sequence complementary to a sequence consisting of at least 20 consecutive nucleotides of an untranslated region of an RNA molecule transcribed or produced from said nucleic acid of interest.

42. The chimeric DNA molecule of claim 17 wherein the target-specific antisense nucleotide sequence consists of at least 20 consecutive nucleotides having 100% sequence identity to a sequence complementary to a sequence consisting of at least 20 consecutive nucleotides of an untranslated region of an RNA molecule transcribed or produced from said nucleic acid of interest.

43. The plant cell of claim 25, wherein the target-specific antisense nucleotide sequence consists of at least 20 consecutive nucleotides having 100% sequence identity to a sequence complementary to a sequence consisting of at least 20 consecutive nucleotides of an untranslated region of an RNA molecule transcribed or produced from said nucleic acid of interest.

44. The transgenic plant of claim 34, wherein the target-specific antisense nucleotide sequence consists of at least 20 consecutive nucleotides having 100% sequence identity to a sequence complementary to a sequence consisting of at least 20 consecutive nucleotides of an untranslated region of an RNA molecule transcribed or produced from said nucleic acid of interest.

45. The method of claim 1, wherein said spacer nucleotide sequence consists of 4 nucleotides to 200 nucleotides.

46. The chimeric DNA molecule of claim 17, wherein said spacer nucleotide sequence consists of 4 nucleotides to 200 nucleotides.

47. The plant cell of claim 25, wherein said spacer nucleotide sequence consists of 4 nucleotides to 200 nucleotides.

48. The transgenic plant of claim 34, wherein said spacer nucleotide sequence consists of 4 nucleotides to 200 nucleotides.

* * * * *

SEQUENCE LISTING

```
<160> NUMBER OF SEQ ID NOS: 6

<210> SEQ ID NO 1
<211> LENGTH: 322
<212> TYPE: DNA
<213> ORGANISM: Artificial Sequence
<220> FEATURE:
<223> OTHER INFORMATION: Description of Artificial Sequence: Barley
      yellow dwarf virus satellite RNA (minus strand)

<400> SEQUENCE: 1
tatccacgaa ataggaagtc gatcttttgc aagagtagcg aactcgttgc tctgtgaaag      60
attgatcgat tgtttccegg tgtctcaagg tgcgtacctt gactgatgag tccgaaagga     120
cgaaacacca gtgttccagt gcgagcgaaa gctcgggctg aacaaacacg taaagcaagt     180
ctcctcattc gaaagagtgg tggccacctg gtggtgccac aattggagat ctttacttcg     240
gtggatttct gtatctattt gttggacgag gcaccagcct tctagtccgc gcggatacgt     300
cgtcagacag tacgcgctct gt                                              322

<210> SEQ ID NO 2
<211> LENGTH: 322
<212> TYPE: DNA
<213> ORGANISM: Artificial Sequence
<220> FEATURE:
<223> OTHER INFORMATION: Description of Artificial Sequence: Barley
      Yellow Dwarf virus satellite RNA (positive strand)
```

```
<400> SEQUENCE: 2
acagagcgcg tactgtctga cgacgtatcc gcgcggacta gaaggctggt gcctcgtcca      60
acaaatagat acagaaatcc accgaagtaa agatctccaa ttgtggcacc accaggtggc     120
caccactctt tgaagtgagg agacttgctt tacgtgtttg ttcagcccga gctttcgctc     180
gcactggaac actggtgttt cgtcctttcg gactcatcag tcaaggtacg caccttgaga     240
caccgggaaa caatcgatca atctttcaca gagcaacgag ttcgctactc ttgcaaaaga     300
tcgacttcct atttcgtgga ta                                              322

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence:
      oligonucleotide; PCR primer SATPR1

<400> SEQUENCE: 3
cgcggatccg ttaacagagc gcgtactgtc tg                                    32

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence:
      oligonucleotide PCR primer SATPR2

<400> SEQUENCE: 4
gccgagctca agtctcctca cttcaaag                                         28

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence:
      oligonucleoitde PCR primer SATPR2

<400> SEQUENCE: 5
gcgctgcagc tttacgtgtt tgttcagc                                         28

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence:
      oligonucleotide PCR primer SATPR4

<400> SEQUENCE: 6
gcgggatccg atatccacga aataggaagt cg                                    32
```